(12) United States Patent
Bonham et al.

(10) Patent No.: US 10,610,677 B2
(45) Date of Patent: Apr. 7, 2020

(54) UROLOGICAL SYSTEM THAT INCLUDES CONNECTOR WITH INTEGRATED NON-RETURN CHECK VALVE FOR EXTENSION TUBING AND UROLOGY COLLECTION SYSTEMS

(71) Applicant: Celeste V. Bonham, Fredericksburg, TX (US)

(72) Inventors: Celeste V. Bonham, Fredericksburg, TX (US); Philip N. Smith, Monterey Park, CA (US)

( * ) Notice: Subject to any disclaimer, the term of this patent is extended or adjusted under 35 U.S.C. 154(b) by 9 days.

(21) Appl. No.: 15/434,040

(22) Filed: Feb. 15, 2017

(65) Prior Publication Data

US 2017/0173322 A1 Jun. 22, 2017

Related U.S. Application Data

(63) Continuation-in-part of application No. 14/281,524, filed on May 19, 2014, now abandoned.
(Continued)

(51) Int. Cl.
*A61M 39/10* (2006.01)
*A61M 39/24* (2006.01)
(Continued)

(52) U.S. Cl.
CPC ............ *A61M 39/24* (2013.01); *A61M 39/10* (2013.01); *A61M 39/162* (2013.01);
(Continued)

(58) Field of Classification Search
CPC .. A61M 2039/2406; A61M 2039/2446; A61M 2039/248; A61M 2202/0496;
(Continued)

(56) References Cited

U.S. PATENT DOCUMENTS

| 2,867,213 A | * | 1/1959 | Thomas, Jr. | .......... | A61M 39/24 |
| | | | | | 137/559 |
| 3,848,603 A | | 11/1974 | Throner | | |

(Continued)

*Primary Examiner* — Adam Marcetich
(74) *Attorney, Agent, or Firm* — Eric Kelly

(57) ABSTRACT

A connector-with-integrated-check-valve for minimizing microbial migration to catheter-tubing is formed from three parts: a connector-for-catheter-tubing that is hollow and with an internal valve seat; an elastomer disc shaped gate; and a connector-for-extension-tubing that is hollow and with support-surfaces. When one end of the connector-for-catheter-tubing is attached to one end of the connector-for-extension-tubing, a pocket is formed where the seat is disposed opposite and facing the support-surfaces; the gate is disposed within this pocket; such that when the gate contacts this seat due to urine backflow (reflux), the connector-with-integrated-check-valve is closed to such urine backflow; and where a remaining end of the connector-for-catheter-tubing is attachable to catheter-tubing; and where a remaining end of the connector-for-extension-tubing is attachable to the extension-tubing, such that there is a continuous urine flow path from the catheter-tubing, to the connector-with-integrated-check-valve when open, and to the extension-tubing.

21 Claims, 26 Drawing Sheets

Related U.S. Application Data

(60) Provisional application No. 62/389,288, filed on Feb. 22, 2016.

(51) Int. Cl.
*F16K 15/02* (2006.01)
*A61M 39/16* (2006.01)
*F16K 27/02* (2006.01)

(52) U.S. Cl.
CPC ........ *F16K 15/023* (2013.01); *F16K 27/0209* (2013.01); *A61M 2039/2406* (2013.01); *A61M 2039/248* (2013.01); *A61M 2039/2446* (2013.01); *A61M 2202/0496* (2013.01); *A61M 2205/0205* (2013.01); *A61M 2207/00* (2013.01); *Y10T 29/49817* (2015.01); *Y10T 29/49826* (2015.01)

(58) Field of Classification Search
CPC ...... A61M 2205/0205; A61M 2207/00; A61M 39/10; A61M 39/162; A61M 39/24; Y10T 29/49817; Y10T 29/49826; F16K 15/028; F16K 15/023
See application file for complete search history.

(56) References Cited

U.S. PATENT DOCUMENTS

| | | | | |
|---|---|---|---|---|
| 4,023,607 | A | 5/1977 | Jensen | |
| 4,160,383 | A * | 7/1979 | Rauschenberger | A61F 5/441 137/588 |
| 4,165,764 | A * | 8/1979 | Grandclement | F16K 7/12 137/504 |
| 4,354,492 | A * | 10/1982 | McPhee | A61M 5/40 137/528 |
| 4,373,550 | A * | 2/1983 | Yelich | F16K 15/00 137/516.27 |
| 4,607,660 | A * | 8/1986 | Bennitt | F16K 15/023 137/512.1 |
| 4,655,248 | A * | 4/1987 | Chalaire | F16K 15/021 137/515.7 |
| 4,693,712 | A | 9/1987 | Bates | |
| 4,700,741 | A * | 10/1987 | Murphy | F16K 15/044 137/539 |
| 4,784,654 | A * | 11/1988 | Beecher | A61F 5/455 604/329 |
| 5,395,348 | A * | 3/1995 | Ryan | A61M 39/14 251/149.1 |
| 5,443,723 | A * | 8/1995 | Stankowski | B01D 29/05 210/232 |
| 5,727,594 | A * | 3/1998 | Choksi | A61M 39/24 137/537 |
| 5,741,240 | A | 4/1998 | Olsen | |
| 5,749,861 | A * | 5/1998 | Guala | A61M 39/26 251/149.1 |
| 5,771,935 | A * | 6/1998 | Myers | A61M 39/24 137/859 |
| 6,044,859 | A * | 4/2000 | Davis | A61M 39/24 137/15.19 |
| 6,050,934 | A | 4/2000 | Mikhail | |
| 6,183,437 | B1 | 2/2001 | Walker | |
| 6,203,321 | B1 * | 3/2001 | Helmer | A61C 17/04 433/95 |
| 6,390,130 | B1 * | 5/2002 | Guala | A61M 39/24 137/859 |
| 6,439,538 | B1 * | 8/2002 | Ito | A61B 5/031 251/176 |
| 6,471,680 | B1 | 10/2002 | Cawood | |
| 6,736,803 | B2 | 5/2004 | Cawood | |
| 7,766,899 | B2 | 8/2010 | Bolmsjo | |
| 2003/0032944 | A1 | 2/2003 | Cawood | |
| 2004/0089349 | A1 * | 5/2004 | Meyer | F16K 15/142 137/517 |
| 2005/0004525 | A1 | 1/2005 | Sarangapani | |
| 2005/0048124 | A1 | 3/2005 | Sarangapani | |
| 2005/0059929 | A1 | 3/2005 | Bolmsjo | |
| 2005/0257838 | A1 * | 11/2005 | Enerson | F16K 15/023 137/528 |
| 2006/0027270 | A1 * | 2/2006 | Truitt | A61M 39/02 137/843 |
| 2007/0129690 | A1 | 6/2007 | Rosenblatt | |
| 2007/0163664 | A1 * | 7/2007 | Mijers | F16K 15/144 137/859 |
| 2007/0244423 | A1 | 10/2007 | Zumeris | |
| 2007/0282283 | A1 * | 12/2007 | Kaern | A61F 5/4405 604/323 |
| 2008/0169444 | A1 * | 7/2008 | Guala | A61M 39/24 251/331 |
| 2009/0326483 | A1 | 12/2009 | Green | |
| 2011/0108147 | A1 * | 5/2011 | Carmody | A61M 39/24 137/843 |
| 2011/0186151 | A1 * | 8/2011 | Sparazynski | B60T 17/02 137/526 |
| 2012/0042427 | A1 | 2/2012 | Messier | |
| 2013/0245496 | A1 | 9/2013 | Wells | |
| 2013/0253479 | A1 | 9/2013 | Su | |
| 2013/0255061 | A1 | 10/2013 | Burkholz | |
| 2014/0014213 | A1 * | 1/2014 | Hull | F16K 15/023 137/883 |
| 2014/0110003 | A1 * | 4/2014 | Chambers | F16K 15/18 137/852 |
| 2014/0200558 | A1 * | 7/2014 | McDaniel | F16K 27/0227 604/544 |
| 2014/0299212 | A1 * | 10/2014 | Colm | A61M 39/24 137/843 |
| 2015/0176715 | A1 * | 6/2015 | Huang | F04B 33/005 137/528 |
| 2015/0352349 | A1 * | 12/2015 | Carmody | A61M 5/165 137/544 |
| 2016/0040791 | A1 * | 2/2016 | Sasaki | F16K 27/0209 137/528 |
| 2016/0208940 | A1 * | 7/2016 | Vargas Fonseca | A61M 5/16804 |

* cited by examiner

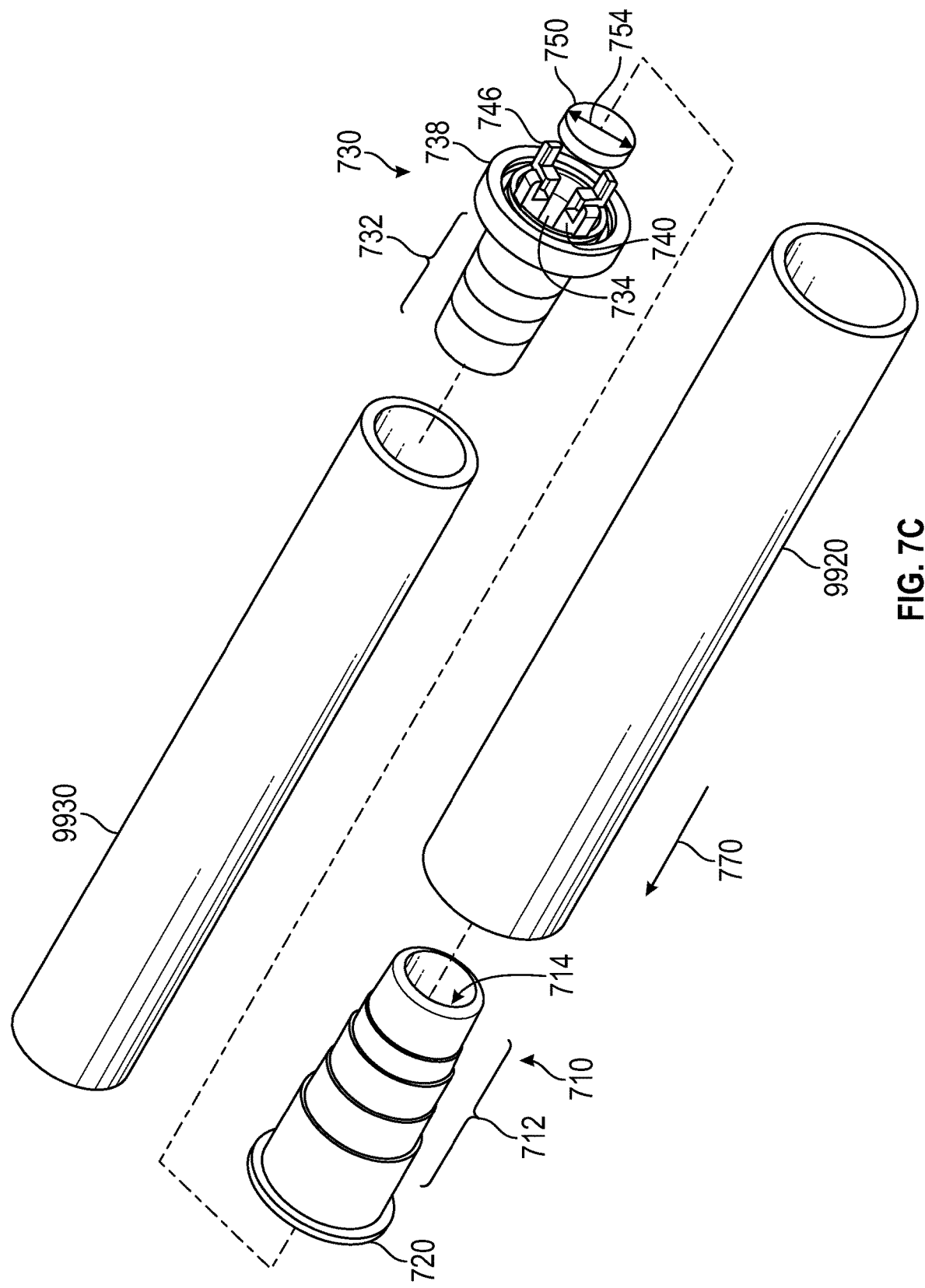

UROLOGICAL SYSTEM THAT INCLUDES CONNECTOR WITH INTEGRATED NON-RETURN CHECK VALVE FOR EXTENSION TUBING AND UROLOGY COLLECTION SYSTEMS

PRIORITY NOTICE

The present patent application is a continuation-in-part (CIP) of U.S. non-provisional patent application Ser. No. 14/281,524 filed on May 19, 2014 and claims priority to said U.S. non-provisional patent application under 35 U.S.C. § 120. The above-identified patent application is incorporated herein by reference in its entirety as if fully set forth below.

The present application also claims priority under 35 U.S.C. § 119(e) to U.S. Provisional Patent Application Ser. No. 62/389,288 filed on Feb. 22, 2016, the disclosure of which is incorporated herein by reference in its entirety as if fully set forth below.

STATEMENT REGARDING FEDERAL SPONSORSHIP

No part of this invention was a result of any federally sponsored research.

TECHNICAL FIELD OF THE INVENTION

The present invention relates in general to urinary tubing and more specifically to flexible urinary tubing, such as extension tubing, which may comprise various means for minimizing microbial migration in a direction opposite of intended flow. Additionally, a system and a method for forming an anti-reflux extension tubing system with respect to urinary tubing connected to a catheter and urine container are described and disclosed.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

One in five patients admitted to hospitals receive an indwelling urinary catheter (hereinafter, "catheter"). When a patient receives a catheter, and the longer the catheter is placed inside the body, the more likely the patient will develop a urinary tract infection (UTI). Hospital-associated infections (HAIs) are infections acquired during the course of receiving treatment for other conditions within a hospital setting. In the United States according to the Centers for Disease Control and Prevention (CDC) more than four million patients develop HAIs in the United States each year with about 99,000 of such cases resulting in death.

UTIs may be caused by microbes (e.g. bacteria) entering the body through the catheter. The distribution of microbes among patients with hospital-acquired urinary tract-related bloodstream infections may include: *enterococcus, candida, E. coli, klebsiella, staphylococcus*, and the like. According to the ICHP, the urinary tract is the most common site of HAIs and accounts for more than 64% of catherized patients in acute-care hospitals. In 2014, the CDC released a HAI Progress Report stating that among five categories of HAIs, only catheter-associated urinary tract infections (CAUTI) had an increase of incidents. Due to the increase of CAUTIs, the Centers for Medicare and Medicaid Services (CMS) will not allow hospitals to be reimbursed for treating a hospital-acquired CAUTI because nosocomial CAUTIs and are believed to be "reasonably preventable." The cost of treating UTIs could cost U.S. hospitals between $1.6 billion and $7.39 billion annually in lost Medicare reimbursements since treating each CAUTI incident may cost between US$600 to US$2,800 to treat.

Microbes may travel intraluminally in the urinary system at least two ways: (1) suspended and floating microbial cells within the urine (i.e., bacteriuria) where there is backflow (reflux) of infected urine; and (2) by biofilm migration (i.e., colonies of microbial cells that may form layers and attach themselves to surfaces) that may ascend up through the inside of urinary tubing surfaces and into the catheter and potentially enter the patient's body. Research currently suggests that preventing urine backflow (reflux) from entering the catheter and/or incorporating a hurdle or barrier that prevents biofilms from ascending through the urinary collection system would help to mitigate the number of UTIs. Currently, the number of patients developing bacteriuria or UTIs after two and three days is 10% to 30%; while after one week or longer is near 90%, and; long-term catheterization (of one month or more) results in near 100% of patients with bacteriuria or UTIs. Although not all CAUTIs may be prevented, it is believed by the medical community that a substantial number of CAUTIs may be avoided by the proper management of indwelling and external catheters. CMS developed a list of recommendations and guidelines to help reduce UTIs and CAUTIs. One of these recommendations included preventing backflow (reflux) of urine which could contain bacteriuria or other microbes. Furthermore, prevention may be the best way to manage nosocomial UTI, as opposed to focusing on expensive treatment and medicine, which may or may not be effective, as many microbes are becoming increasingly less sensitive and more resistant to antibiotics.

A first and second anti-reflux barrier (e.g., one or more check-valves and/or one or more clamps) within a urinary system (e.g., comprising extension tubing and one or more check-valves) may be beneficial by denying microbes various routes of entry into the patient. If such a system is breached (e.g., by inappropriate opening), then microbes may enter the extension tubing and catheter and travel up into the urethra or body wall of the patient and infect the patient.

To date (circa 2014), the inventor is not aware of any prior art that specifically addresses a device or component that forms an anti-reflux extension tubing system or where such a device or component may prevent urine backflow (reflux) of urine located within urinary extension tubing that connects the urinary indwelling and/or external catheter to the urine bag, or where such a device or component may prevent biofilm migration. Reference should also be made that there are no commercial products currently available that specifically addresses prevention of urine backflow in urinary collection systems, such as the extension tubing, by placing a check-valve inside the urinary extension tubing or within a connector of the extension tubing.

Rather, unrelated prior art consists of inventions for closed-system and anti-reflux system are irrigation connectors, intravenous syringe ports, closed adapters for enteral formula delivery, and needleless IV access ports for small bore luers—i.e., none of this prior art deals with urinary systems.

For example, some such prior art include: preventing backflow for blood and urine specimens (i.e., not urinary collection system) and maintaining a closed-system for irrigation; and of using check-valves in feeding tubes. Such prior art does not incorporate any anti-reflux check-valve within the primary urinary extension tubing running from the indwelling catheter to the urine bag.

Additionally, the prior art may include a check-valve located within a urine bag. This prior art may prevent urine backflow (reflux) from the urine bag into the extension tubing. However, the urine collection system between the urine bag and the patient is vulnerable and presently has no barrier against urine backflow. If there is no anti-reflux valve (i.e., check-valve) present before the catheter to prevent urine backflow, then microbes in the urine may travel from the urine in tubing into the catheter leading to a CAUTI.

There is a need in the art for satisfactorily addressing and reducing the high percentage of UTIs and CAUTIs that occur with current indwelling and/or external urinary catheter use.

It is to these ends that the present invention has been developed.

BRIEF SUMMARY OF THE INVENTION

To minimize the limitations in the prior art, and to minimize other limitations that will be apparent upon reading and understanding the present specification, the present invention may describe a connector-with-integrated-check-valve for minimizing microbial migration to catheter-tubing as well as a system for minimizing microbial migration to the catheter-tubing.

In some embodiments, the connector-with-integrated-check-valve for minimizing microbial migration to catheter-tubing may be formed from three parts: a connector-for-catheter-tubing that is hollow and with an internal valve seat; an elastomer disc shaped gate; and a connector-for-extension-tubing that is hollow and with support-surfaces. When one end of the connector-for-catheter-tubing is attached to one end of the connector-for-extension-tubing, a pocket is formed where the seat is disposed opposite and facing the support-surfaces; the gate is disposed within this pocket; such that when the gate contacts this seat due to urine backflow (reflux), the connector-with-integrated-check-valve is closed to such urine backflow; and where a remaining end of the connector-for-catheter-tubing is attachable to catheter-tubing; and where a remaining end of the connector-for-extension-tubing is attachable to the extension-tubing, such that there is a continuous urine flow path from the catheter-tubing, to the connector-with-integrated-check-valve when open, and to the extension-tubing.

It is an objective of the present invention to provide urinary extension tubing and/or a connector-with-integrated-check-valve that may be capable of minimizing microbial migration in a direction opposite of intended flow, by utilizing the various means discussed herein, specifically in the DETAILED DESCRIPTION OF THE INVENTION section of this specification.

It is another objective of the present invention to provide urinary extension tubing that may be capable of minimizing urine backflow (reflux) from the intended flow of urine within the urinary extension tubing and preventing backflow into a catheter.

It is another objective of the present invention to provide urinary extension tubing that may comprise at least one check-valve positioned within the urinary tubing or within a connector attached to the extension tubing, i.e., a connector-with-integrated-check-valve.

It is another objective of the present invention to provide urinary extension tubing that may comprise at least one biofilm abater positioned within the urinary tubing to minimize biofilm migration across the at least one biofilm abater. See the DETAILED DESCRIPTION OF THE INVENTION section for a discussion of biofilm abaters.

It is another objective of the present invention to provide urinary extension tubing and/or a connector-with-integrated-check-valve, that may comprise at least one wettable region (e.g., a region of urinary tubing inside diameter) treated with an antimicrobial coating lining at least some portions the luminal walls (interior walls) of the urinary tubing to minimize biofilm migration across the at least one wettable region treated with the antimicrobial coating.

It is another objective of the present invention to provide urinary extension tubing that may comprise various connectors, both with and without check-valves, where such connectors may be positioned within the urinary tubing, at the first terminal end, and/or the second terminal end, wherein such connectors (and/or tubing) may be treated (e.g., by coating) with an antimicrobial coating to mitigate against biofilm migration across such connectors treated with the antimicrobial coating.

It is another objective of the present invention to provide a method or series of methods for forming and maintaining an anti-reflux extension tubing system with respect to urinary extension tubing connected to a catheter.

It is yet another objective of the present invention to provide systems for forming and maintaining an anti-reflux extension tubing system with respect to urinary tubing connected to a catheter.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Elements that are known to be common and well understood to those in the industry are not depicted in order to provide a clear view of the various embodiments of the invention.

Note, with respect to the above stated cross-sectional views, cross-sections of the various connectors with integral check-valves, connectors with non-integral check-valves, and check-valves without connectors are not depicted. Cross-section of the various catheter sampling ports are also not depicted.

Note, any breaks depicted in tubing length in the various figures may indicate that the tubing may have a variety of lengths.

Figure 7A:
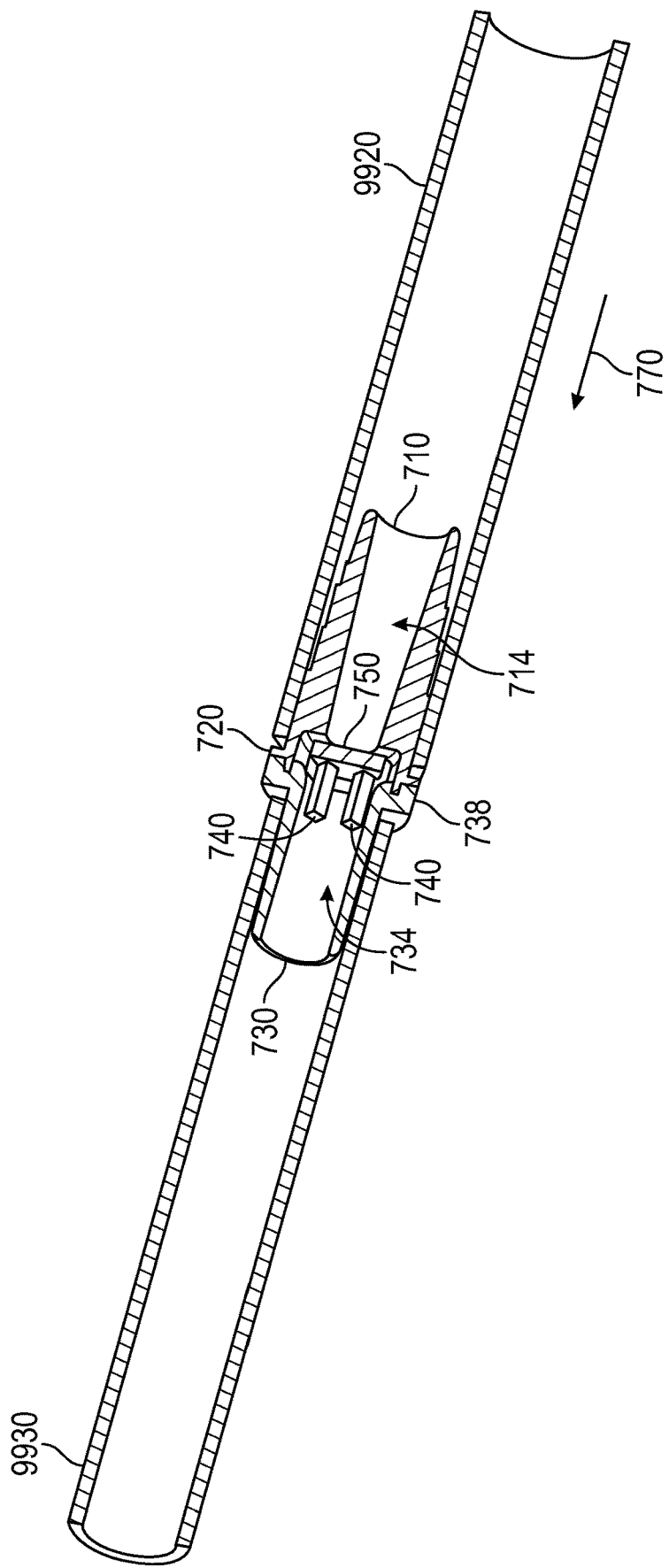

FIG. 7A may depict a perspective and longitudinal cross-sectional view of an embodiment of a connector-with-integrated-check-valve that is attached to catheter-tubing at one end and attached to extension-tubing at the other end.

Figure 7B:
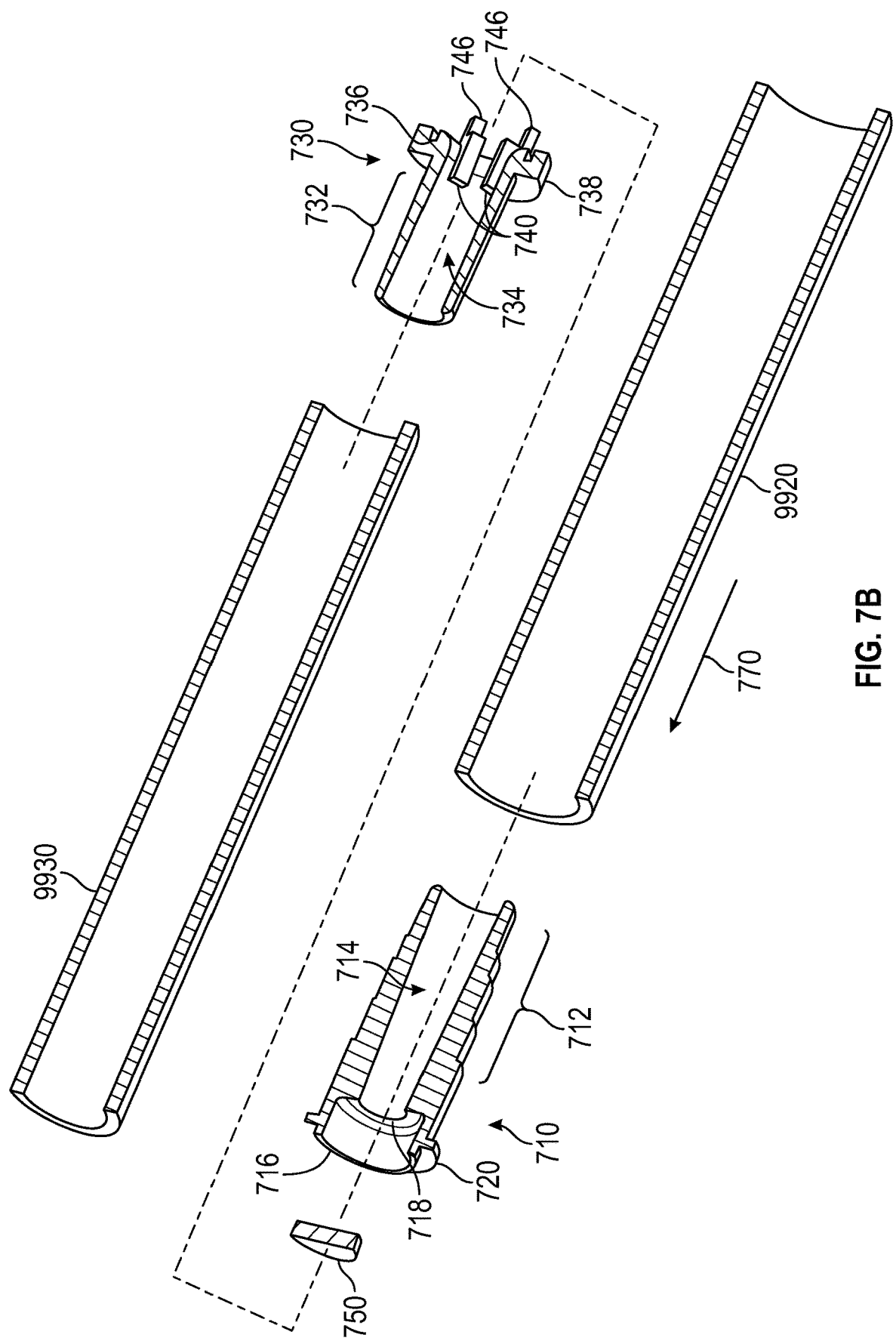

FIG. 7B may depict the same embodiment of FIG. 7A, but shown in an exploded, perspective, and longitudinal cross-sectional view.

FIG. 7C may depict the same embodiment of FIG. 7A, but shown in an exploded and a perspective view.

Figure 7D:
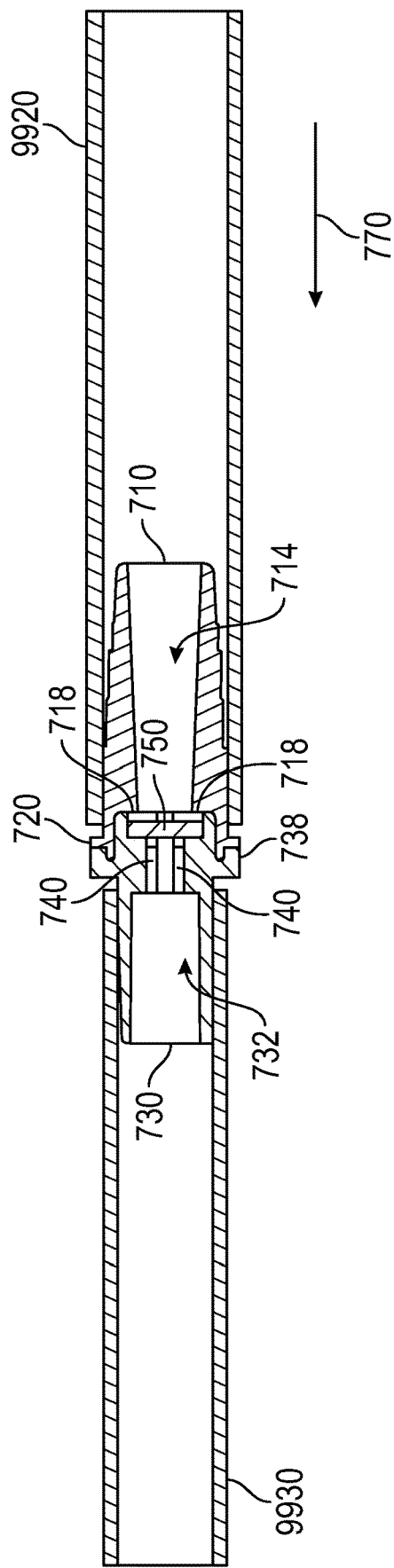

FIG. 7D may depict the same embodiment of FIG. 7A, but shown in a longitudinal cross-sectional view.

Figure 7E:
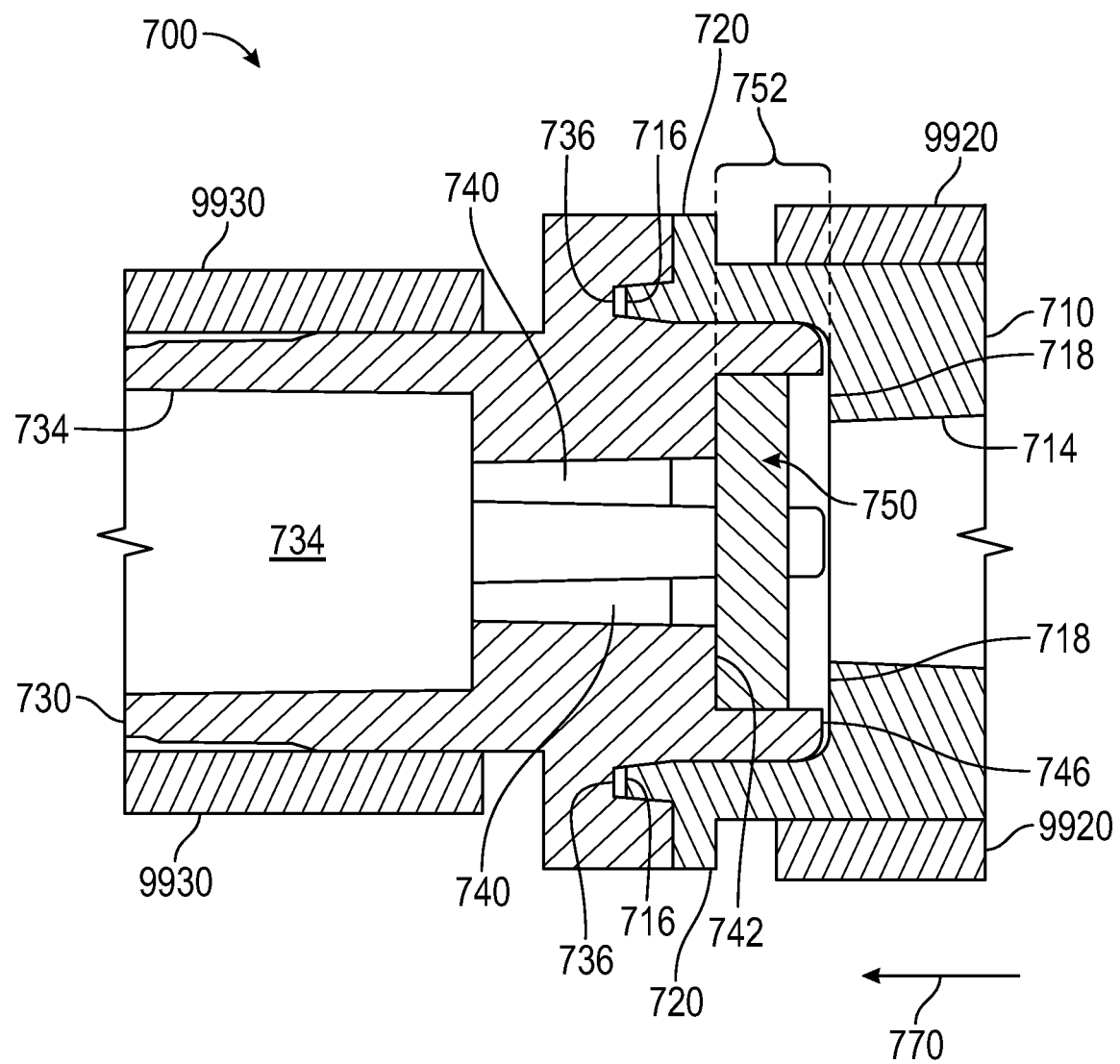

FIG. 7E may be a close up view of the connector-with-integrated-check-valve shown in FIG. 7D, wherein the connector-with-integrated-check-valve may be shown in an open configuration.

Figure 7F:
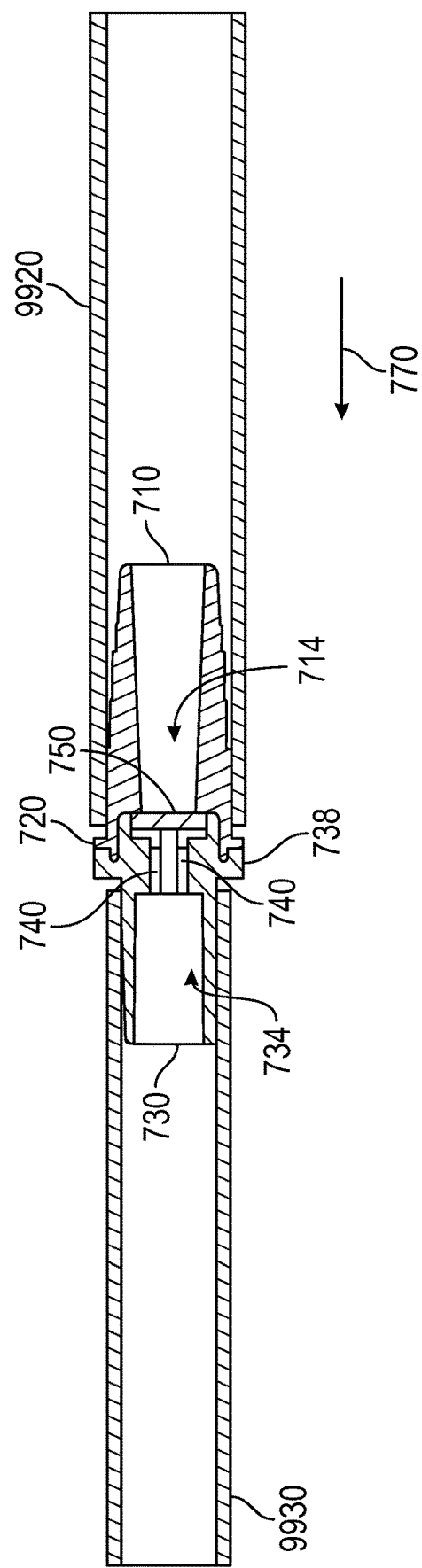

FIG. 7F may depict the same embodiment of FIG. 7A, but shown in a longitudinal cross-sectional view.

Figure 7G:
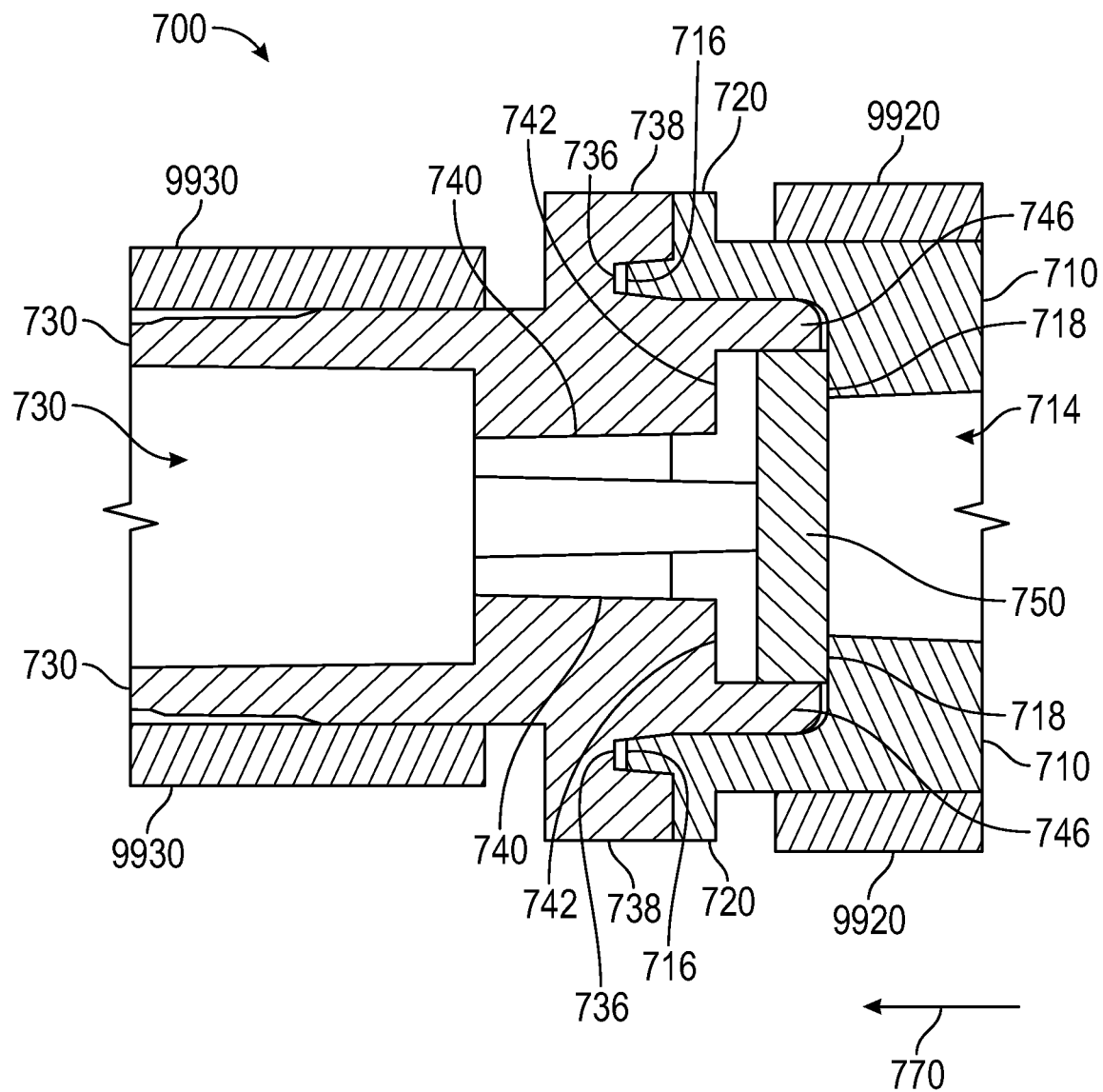

FIG. 7G may be a close up view of the connector-with-integrated-check-valve shown in FIG. 7F, wherein the connector-with-integrated-check-valve may be shown in a closed configuration.

Figure 7H:
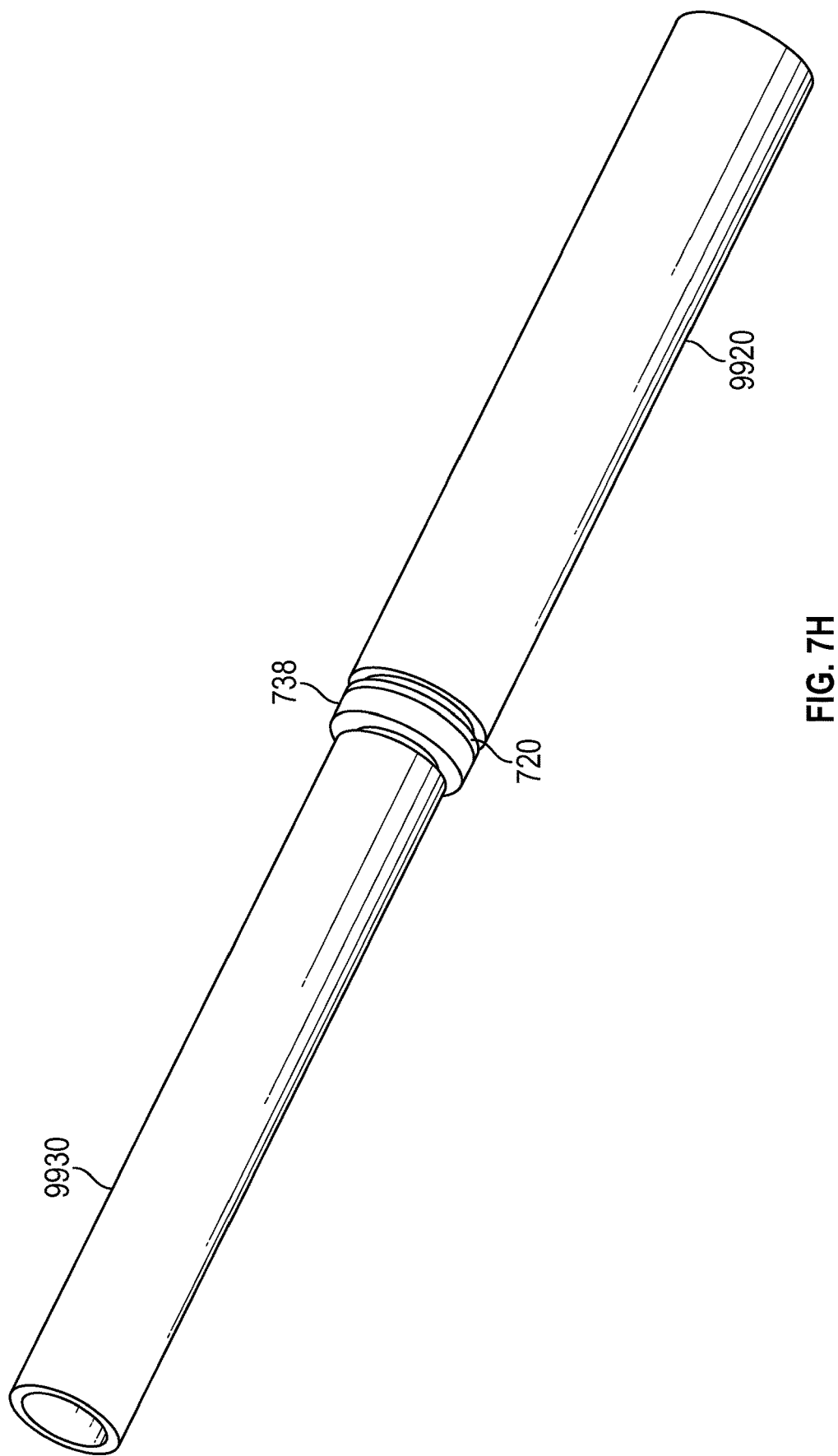
Figure 71:
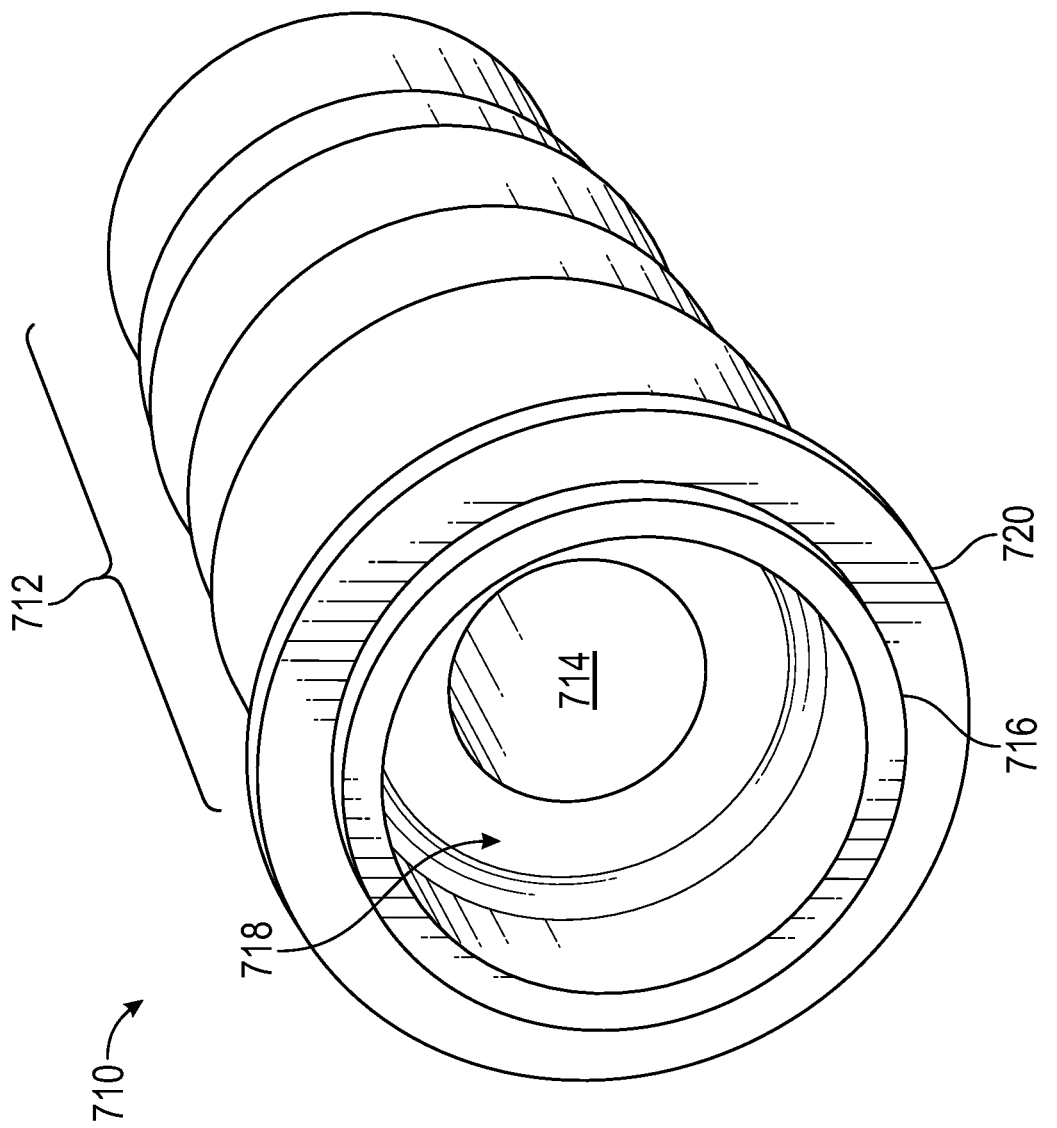

FIG. 7H may depict the same embodiment of FIG. 7A, but shown in a perspective view.

FIG. 7I may show an outlet perspective view of an embodiment of a connector-for-catheter-tubing, which may be a component of the connector-with-integrated-check-valve shown in FIG. 7A.

Figure 7J:
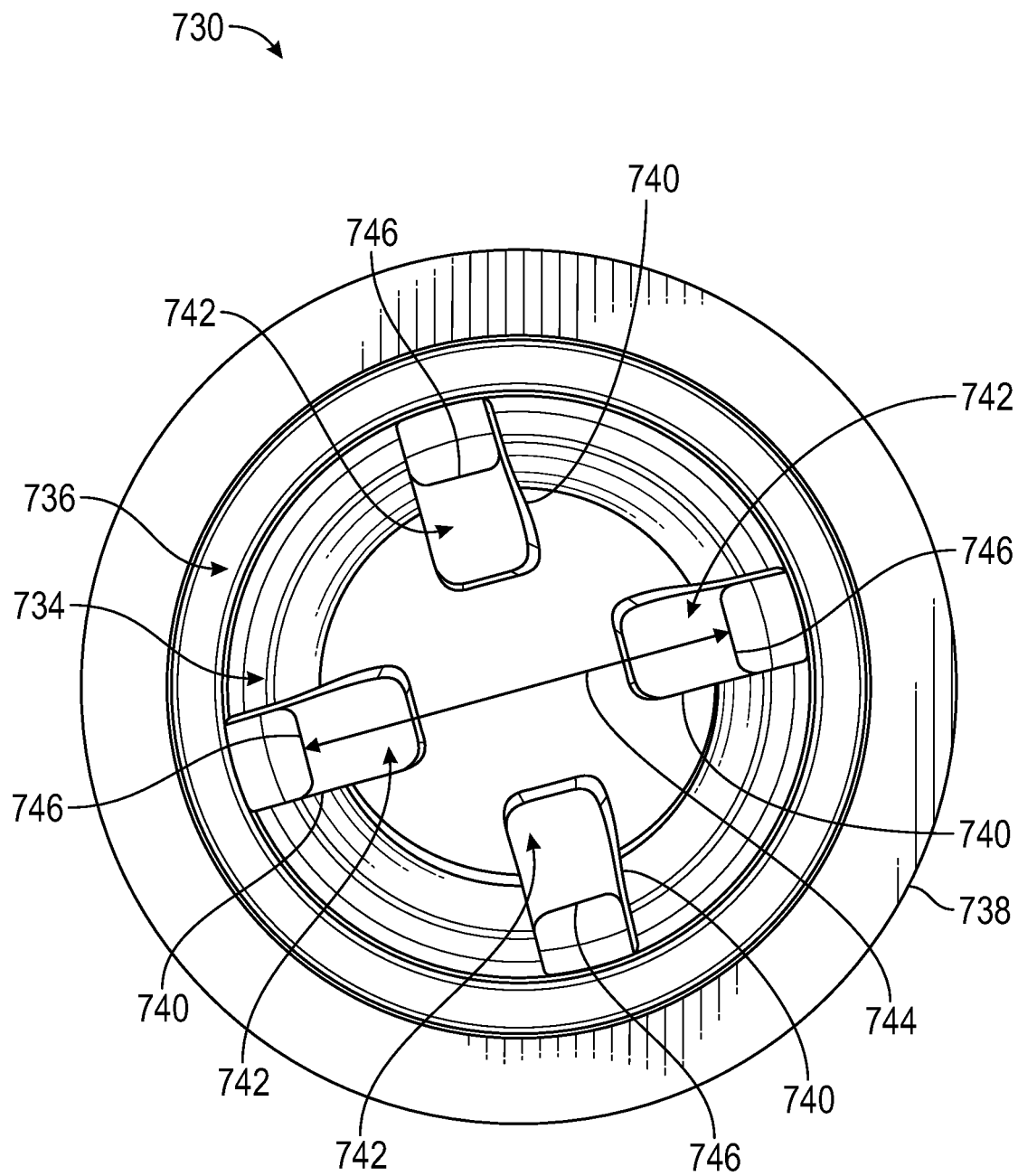

FIG. 7J may show an inlet view of an embodiment of a connector-for-extension-tubing, which may be a component of the connector-with-integrated-check-valve shown in FIG. 7A.

Figure 7K:
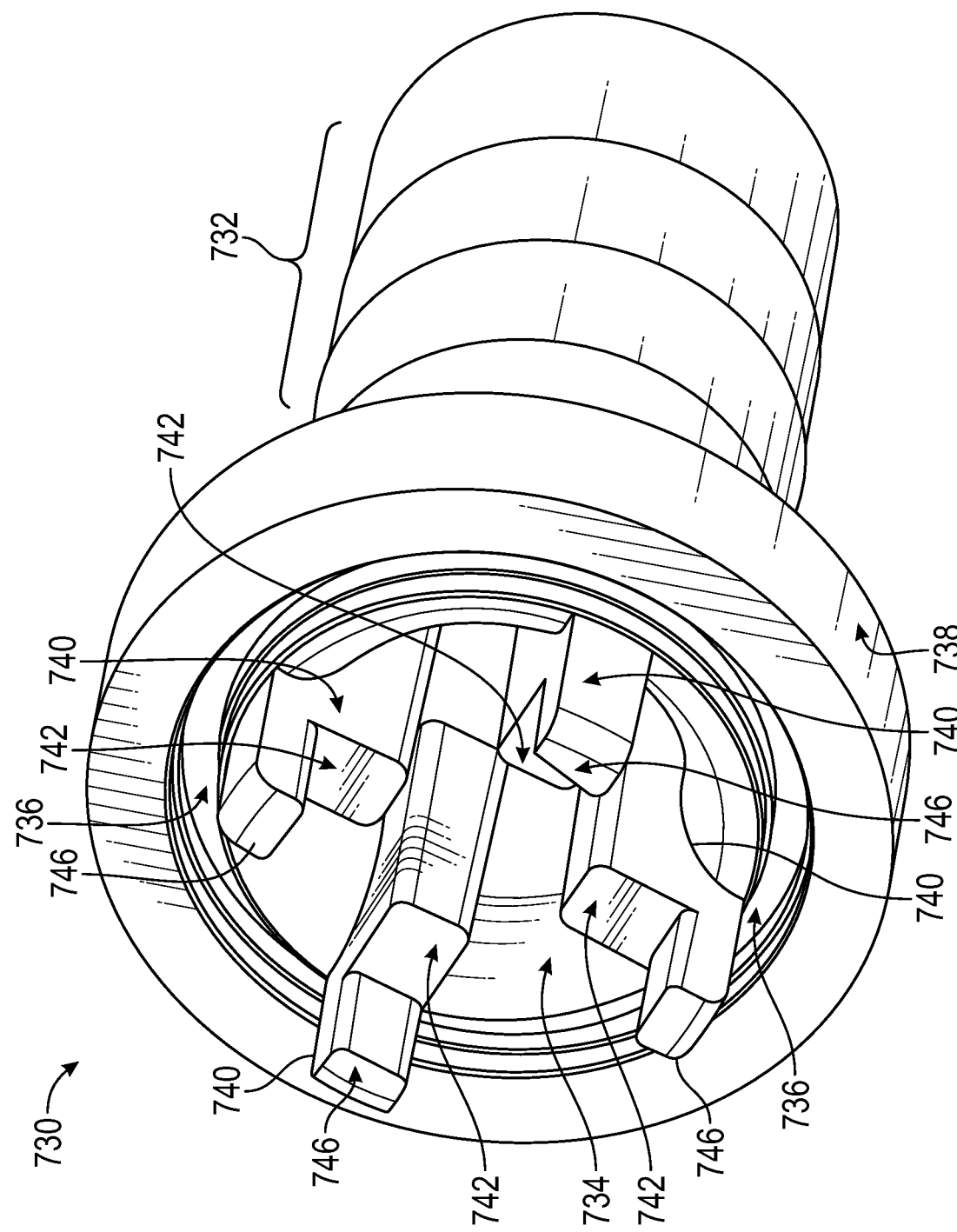

FIG. 7K may depict an inlet perspective view of the connector-for-extension-tubing shown in FIG. 7J.

Figure 8:
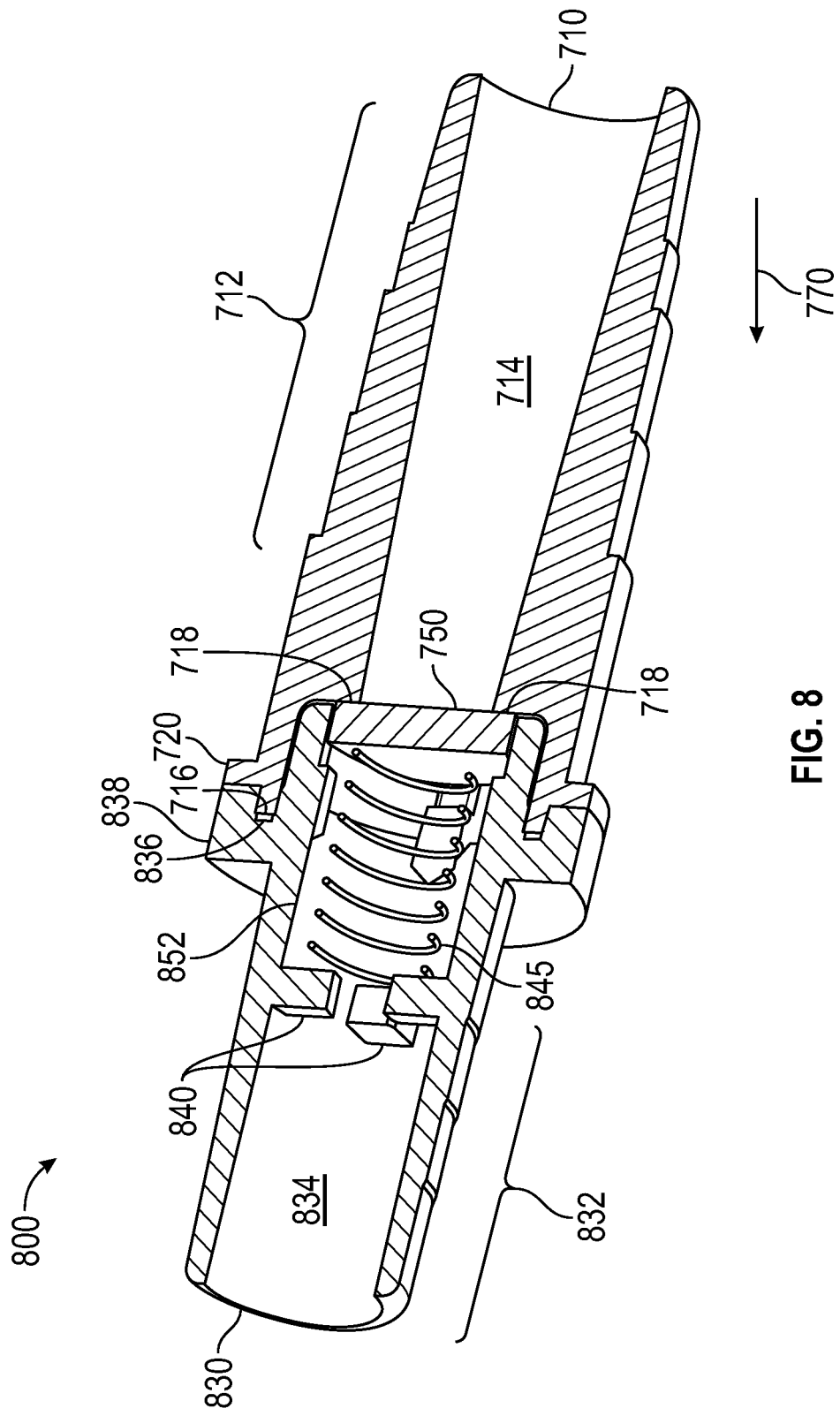

FIG. 8 may depict a perspective and longitudinal cross-sectional view of an embodiment of a connector-with-integrated-check-valve.

Figure 9A:
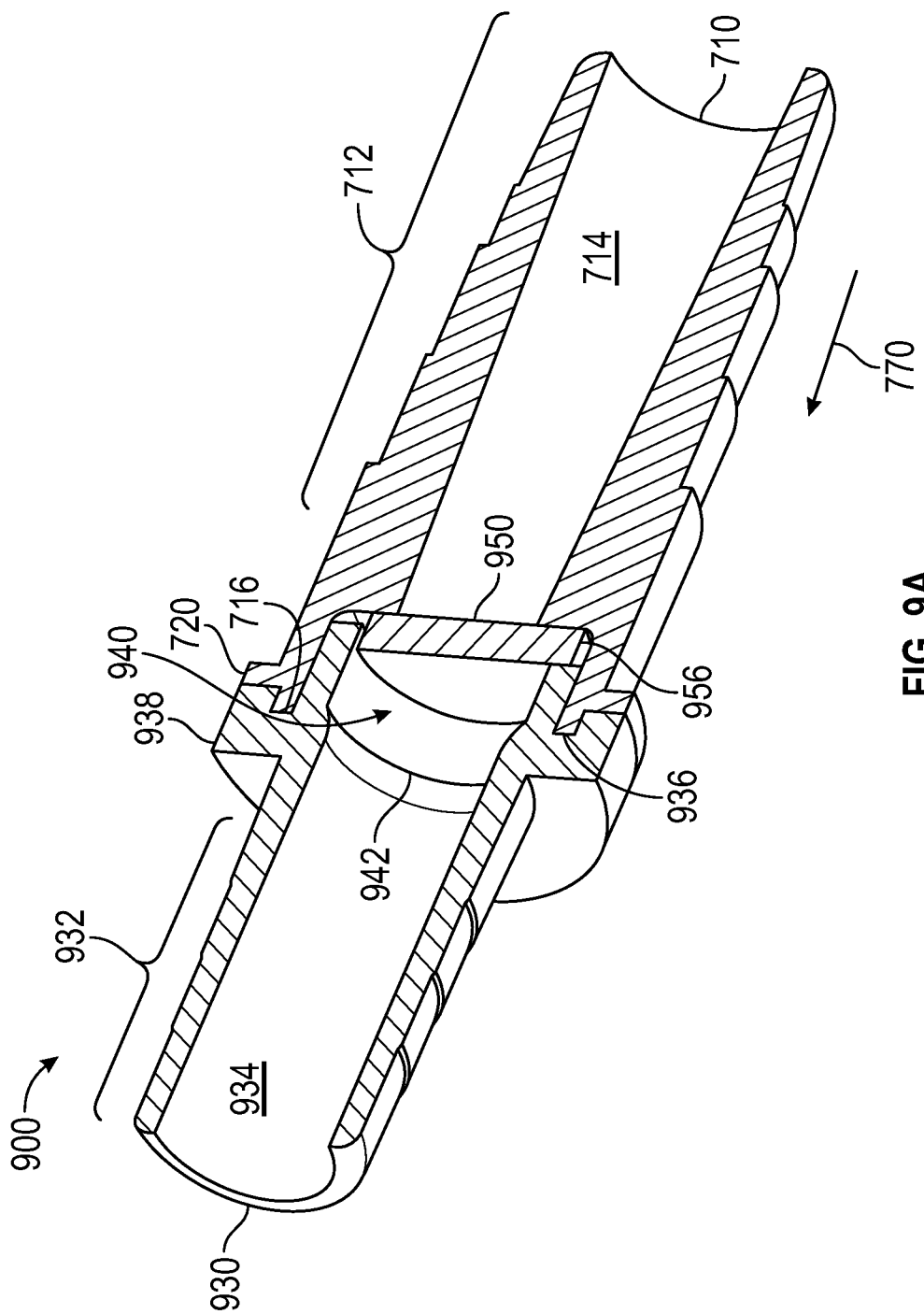

FIG. 9A may depict a perspective and longitudinal cross-sectional view of an embodiment of a connector-with-integrated-check-valve.

Figure 9B:
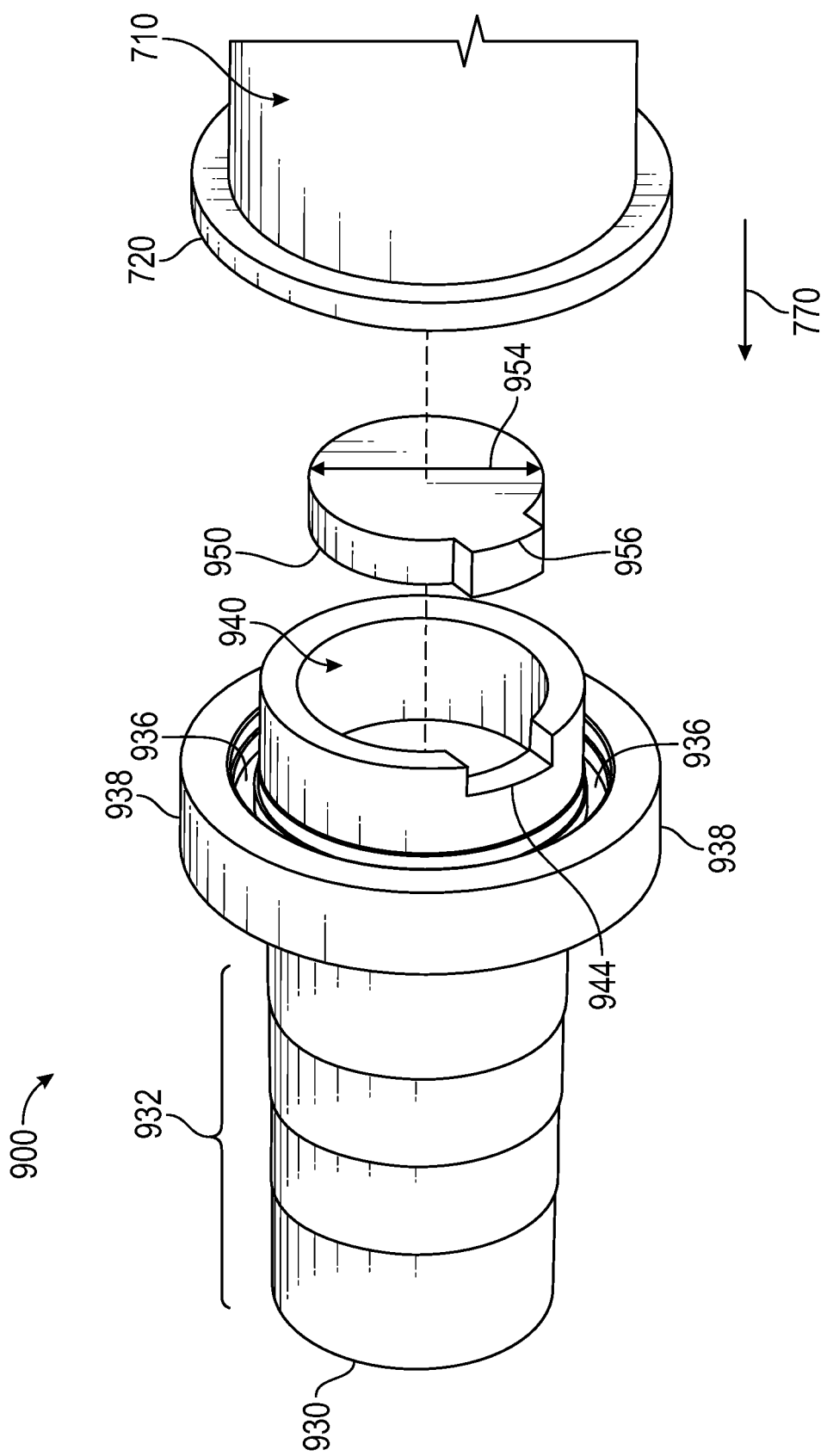

FIG. 9B may depict the same embodiment of FIG. 9A, but shown in an exploded and a perspective view.

REFERENCE NUMERAL SCHEDULE 100 tubing 100
101 first terminal end 101
102 second terminal end 102
103 inside diameter of tubing 103
104 outside diameter of tubing 104
200 tubing embodiment 200
201 tubing embodiment 201
205 connector with check-valve 205
206 coupling sleeve 206
206b tape 206b 300 tubing embodiment 300
301 tubing embodiment with tape 301
307 connector 307
308 check-valve 308
400 tubing embodiment 400
401 tubing embodiment 401
409 first tube 409
410 second tube 410
411 third terminal end 411
412 fourth terminal end 412
500 tubing embodiment 500
501 tubing embodiment 501
601 check-valve pushed into place embodiment 601
602 tubing embodiment 602
603 tubing embodiment 603
605 check-valve 605
613 biofilm abater 613
613a outside diameter 613a
621 tubing embodiment 621
622 inside surface region 622
631 tubing embodiment 631
632 sampling port 632
633 linear distance 633
641 tubing embodiment 641
642 graphical indicator 642
651 tubing embodiment 651
700 connector-with-integrated-check-valve 700
710 connector-for-catheter-tubing 710
712 first-barb-region 712
714 first-hollow-core 714
716 mating-end 716
718 seat 718
720 central-flange 720
730 connector-for-extension-tubing 730
732 second-barb-region 732
734 second-hollow-core 734
736 complimentary-mating-end 736
738 flange 738
740 catch-arms 740
742 support-surface 742
744 receiving-distance 744
746 posts 746
750 gate 750
752 pocket 752
754 gate-outside-diameter 754
770 desired-direction 770
800 connector-with-integrated-check-valve 800
830 connector-for-extension-tubing 830
832 second-barb-region 832
834 second-hollow-core 834
836 complimentary-mating-end 836
838 flange 838
840 spring-stops 840
845 closing-spring 845
852 pocket 852
900 connector-with-integrated-check-valve 900
930 connector-for-extension-tubing 930
932 second-barb-region 932
934 second-hollow-core 934
936 complimentary-mating-end 936
938 flange 938
940 pocket 940
942 stop 942
944 hinge-receiver 944
950 gate 950
954 gate-outside-diameter 954
956 hinge 956

9915 catheter 9915
9917 catheter exit port 9917
9901 urine bag 9901
9901a leg urine bag 9901a
9901b bed urine bag 9901b
9902 urine bag connector 9902
9910 patient 9910
9920 catheter-tubing 9920
9930 extension-tubing 9930

DETAILED DESCRIPTION OF THE INVENTION

Various embodiments of urinary tubing configured to minimize microbial migration in a direction opposite of intended flow are described and disclosed. A system and a method for forming and maintaining a closed-system with respect to urinary tubing connected to a catheter are also described and disclosed.

Before turning to a discussion of the invention's various structures, disclosures regarding various definitions and functional objectives of the inventive structures are disclosed. "Intended flow," "microbe, "microbial," "antimicrobial," "system," "closed-system," and "tubing" are all defined below and in turn.

An example of "intended flow" may be a flow of urine beginning from a patient's urethra (or bladder or kidney) and flowing into and through a urinary catheter (through an inside diameter), then into urinary tubing (through an inside diameter), and finally into a urine bag (e.g., leg or bed). Such intended flow is generally accomplished by the catheter being placed within the patient's urethra (or bladder or kidney), followed by the urinary tubing connected to an exit port of the catheter, and then with the urine bag connected at a remaining terminal end of the urinary tubing, and where the intended flow may be accomplished by each subsequent component being placed below the immediately prior component, i.e., to facilitate flow downhill. Intended flow of urine may be in a same direction of flow as desired-direction 770. Any urine flow opposite of this intended flow direction is known as "backflow" or "reflux." And a primary objective of this invention is to mitigate against microbes migrating in the direction opposite of the intended flow. For example, one way to minimize undesirable microbe migration, may be to prevent or mitigate against fluid (e.g., urine) backflow (reflux), since such fluid may be carrying microbes.

However, regardless of fluid flow, microbes may migrate against the direction of intended flow by forming a biofilm on a surface of the inside of urinary tubing and then said biofilm growing (migrating) in the direction opposite of intended flow. Such surface growth of microbes may generally be facilitated by the microbes attaching to a wettable surface and then growing on the wettable surface. Thus, a second way to minimize undesirable microbe migration may be to inhibit the growth of microbes on such surfaces of the tubing, especially wettable surfaces of the tubing. Another way to minimize microbe migration into the catheter may be to block growth of microbes. Additionally, a fourth way to minimize undesirable microbe migration may be to inhibit attachment of microbes on certain surfaces of the tubing.

Note, in this specification, "microbes" and "microbial" refers to a variety of micro-organisms which may comprise: bacteria, fungi (e.g., yeast), viruses, protozoans, and the like. Microbes may be floating freely and/or suspended within a fluid, including fluid flowing within tubing. Microbes attached to a surface may form a colony comprising many individual microbial cells, i.e., a biofilm. The term, "biofilm" refers to at least one microbial cell that has attached itself to a surface, i.e., a biofilm may be a microbial colony of many microbial cells attached to a surface.

The term, "antimicrobial" as used in this specification may refer to minimizing microbe migration in a direction opposite of intended flow. Functionally, this invention may provide for at least three mechanisms to this desired objective of providing an antimicrobial tubing and system, where those three mechanisms may be: (1) minimizing fluid backflow (reflux); (2) minimizing microbe growth; (3) preventing microbe growth into the catheter; and (4) minimizing microbe attachment to surfaces, particularly to wettable surfaces. As used in this specification, the term "mitigate" may be synonymous with "abate" and may include and encompasses the terms "prevent" and "inhibit."

In some embodiments, a "system" as used in this specification may comprise: a length of urinary extension tubing and at least one connector-with-integrated-check-valve that is connected to the length of urinary extension tubing. In some embodiments, a system may comprise: a catheter, a length of urinary extension tubing, and at least one connector-with-integrated-check-valve that is connected to the length of urinary extension tubing. In some embodiments, a system may comprise: a catheter, a length of urinary tubing, and a urine bag. In embodiments, a system may comprise: a patient, a catheter, and a length of urinary tubing. In embodiments, a system may comprise: a patient, a catheter, a length of urinary tubing, and a urine bag. In some of the above systems, the system may further comprise at least one connector-with-integrated-check-valve that is connected to the length of urinary extension tubing. In some of the above systems, the urinary extension tubing may further comprise some additional structures (e.g., check-valves), some with various antimicrobial structures and functions, as further disclosed and discussed below. In some embodiments, the system may be an anti-reflux extension tubing system.

This invention may comprise various embodiments of such tubing (e.g., urinary tubing as disclosed herein). This invention may also comprise the various systems, wherein such systems may comprise the tubing and the catheter. In other words, the urinary tubing as the invention may not comprise the catheter; but, the system as the invention may comprise the catheter in some embodiments.

With respect to the catheter, such catheters may comprise both indwelling and external catheters. Indwelling catheters may comprise Foley (i.e., inserted into the urethra), suprapubic (inserted into abdomen or bladder), and nephrostomy (e.g., inserted in one or both kidneys). External catheters may comprise condom catheters and female external collection systems.

With respect to the catheter, a connection between the catheter and the extension tubing may be located at the catheter's "exit port." Such an exit port may also be referred to as a "drainage port."

A "closed-system" may refer to how the system may be formed and maintained isolated, i.e., kept physically separated, from components outside of the system. It may be desirable to maintain such systems as closed to help prevent infection, including urine backflow (reflux), from microbes entering the system and making their way into a patient.

A closed-system may be formed by maintaining the following connected components, with at least three points of connections (or points of being sealed from outside influence): (1) a catheter properly connected to a patient's urethra (or bladder or kidney); (2) a proper connection between the catheter's exit port and a terminal end of urinary extension tubing (e.g., a first terminal end); and (3) the remaining terminal end (e.g., second terminal end) of the urinary tubing being connected to a urine bag, or otherwise being sealed (e.g., taped, capped off or clamped shut). Each of these three points of connection may be a source of breach to render an otherwise closed-system into an open system. For example, if the catheter becomes disengaged from the patient's urethra, the system may then be open and microbes may then enter into the human body through the urethra. Another example: if the catheter exit port becomes disengaged from a terminal end of tubing (e.g., a first terminal end), then microbes may enter the catheter into what may now be an open system. This connection of catheter and extension tubing may be taped to avoid unintended disconnect. With respect to the remaining terminal end of tubing (e.g., second terminal end), when such a terminal end is properly connected to a urine bag, and the other two connections are in place, then the system may be closed and no urine backflow (reflux) can enter the tubing due to the check valve (anti-reflux) in the urine bag. But unless some additional step or mechanism is utilized when the urine bag is disengaged from the urinary extension tubing, for example, to replace the urine bag, the system may be open and microbes may then enter the system through the second terminal end of the urinary extension tubing because the remaining terminal end of tubing (e.g., second terminal end) is now open to the external environment since the means of prevention of urine backflow (reflux) is located inside the urine bag that has been removed. This invention, in its various embodiments, may provide structure to maintain the system as closed even when the tubing is disconnected from the urine bag, such as, but not limited to use of a clamp or a second check-valve (that may be closed in its default operational configuration) inside of the urinary extension tubing.

"Tubing" as used in this specification may have several different meanings. Functionally, tubing may be a conduit for transporting a material from one point to another point. For example, that material may be a fluid, such as urine. Structurally, tubing in a traditional sense may comprise an elongated hollow member (e.g., a cylinder) with at least one length (with at least two terminal ends), an outside diameter, an inside diameter, and a wall thickness (defined by the difference in outside and inside diameters). The length of tubing may generally be linear, but could form other shapes, such as a "Y" shape.

Tubing in this invention may further comprise additional structure such as: various connectors, both with and without check-valves; various check-valves, both with and without connectors; biofilm abaters; and antimicrobials coatings: of tubing surfaces, of connectors, and of check-valves. Tubing as used in this specification may be flexible tubing, i.e., as opposed to rigid tubing. Tubing as used in this specification may be medical grade tubing. Medical tubing may be sub-divided into urinary tubing, specifically extension tubing (e.g., extension-tubing 9930), for the transport of urine from a catheter to a urine bag. Tubing as used herein may be described as flexible urinary tubing or flexible urinary extension tubing (e.g., extension-tubing 9930). Tubing may run from an exit port of the catheter directly to the urine bag, i.e., a primary length of tubing. Tubing as used herein may be described as flexible indwelling catheter tubing (e.g., catheter-tubing 9920). The length of tubing may vary to accommodate a leg bag or longer to accommodate the distance between the catheter (or patient) and a bed bag. However, the length of tubing may be predetermined.

In various embodiments, tubing may be substantially constructed of various polymers. The polymers may be suitable for tubing extrusion, injection molding, ultrasonic bonding, solvent bonding, heat welding, and/or chemical adhesives. For example, tubing in the traditional sense of an elongated hollow member with an outside and inside diameter may be efficiently manufactured by extrusion into various lengths. Whereas, tubing in the traditional sense may also be injection molded, but where such a means of manufacture may be more expensive and with limited available lengths compared to extrusion methods of manufacture. Additional, structural components of the tubing (e.g., connectors with or without check-valves, check-valves with or without connectors, biofilm abaters, and coupling sleeves) may be substantially constructed using injection molding.

Such polymers may comprise: urethane (including polyurethanes), rubber (with or without latex), polyvinyl chloride (PVC), silicone, polyethylene (low density and high density), nylon, fluropolymers, polypropylene, acrylonitrile-butadiene styrene (ABS), polycarbonate, acrylic, and/or the like. PVC may be the most common material of construction for flexible medical urinary extension tubing.

With respect to use of "substantially constructed of" in the above materials discussion, such phrasing may be used because various embodiments of tubing may also include some additional non-polymer materials. For example, in various embodiments there may be antimicrobial coatings to certain regions of the tubing, to connectors, to check-valves and/or to biofilm abaters. There may be rigid to semi-rigid plastics used in the check-valves. There may some metal (e.g., stainless steel) used in some components, for example, some check-valves may employ springs made of metal. Biofilm abaters may be constructed of entirely of silver (or silver alloy) or coated with silver (or silver alloy). In some embodiments, adhesives tapes (as a type of coupling sleeve) may also be a component of the tubing. Some solvents may be used for solvent bonding and chemical adhesives may also be utilized in assembly.

Polymer formulations may also comprise other ingredients which increase the cured polymers antimicrobial properties, for example and without limiting the scope of the present invention, including silver within the polymer formulation.

More than one type of polymer may be used within a given embodiment of tubing. For example, and without limiting the scope of the present invention, in various embodiments, the elongated member of the tubing may be substantially constructed of PVC, while a connector, with or without check-valve, may be substantially constructed of HDPE (high density polyethylene) or polycarbonate.

With respect to materials of construction because the tubing may be medical grade tubing, the choice of materials may be limited to polymers which may be manufactured aseptically (e.g., in clean rooms) and then subsequently sterilized without the tubing significantly degrading. Common sterilization methods include steam sterilization via autoclaves, gamma irradiation, ultraviolet exposure, and ethylene oxide (EtO) gas exposure. Gamma irradiation tends to render materials more brittle and steam sterilization may leave behind water vapor which condenses and may facilitate microbial contamination subsequent to the sterilization. Each of the above listed polymers may have various formulations that when cured may appropriately be sterilized by each of these sterilization methods.

Choice of materials may also be limited to polymers which may be field sterilized or sanitized by exposure to various chemicals, such as alcohol (e.g., isopropyl alcohol), bleach, and peroxides. (Field sterilization or sanitization may be sterilization or sanitization done by the user of the product, such as a medical practitioner, as opposed to sterilization that occurs as a step in the manufacturing process.)

Note, with respect to the materials of construction, it is not desired nor intended to thereby unnecessarily limit the present invention by reason of such restricted disclosure.

Now turning to a general discussion of tubing structure, which is further detailed in the discussion of the various figures. In various embodiments, the tubing may comprise a first terminal end and a second terminal end, such that the first terminal end may be disposed opposite of the second terminal end, e.g. located at longitudinal opposing ends. Tubing may be bounded by the first terminal end and the second terminal end.

In some embodiments, the tubing may comprise a wettable region, which may comprise a surface which is wetted when a fluid flows within the tubing. For example, and without limiting the scope of the present invention, common wettable regions may comprise the interior surfaces of the tubing which may comprise an inside diameter of the tubing along a corresponding length of the tubing. Additional wettable regions of the tubing may comprise various interior surfaces of various connectors, with and without check-valves, as well as check-valves without connectors.

An outside diameter of the tubing is generally not a wettable region nor a wettable surface. However, the outside diameter regions immediately proximal of the first terminal end and the second terminal end may be physically so close to wettable regions of the tubing, that such outside diameter regions may also be ideal candidate regions for treating with an antimicrobial coating.

In some embodiments, the tubing (e.g., extension tubing) may comprise a means for minimizing microbial migration in a direction opposite of intended flow. The means for minimizing microbial migration in the direction opposite of intended flow may be selected from one or more of the group comprising: (1) at least one check-valve; (2) at least one biofilm abater; (3) and the wettable region treated with an antimicrobial coating. For example, and without limiting the scope of the present invention, the tubing may comprise one check-valve which has been treated with an antimicrobial coating (or one check-valve with no antimicrobial coating). Any combination of these three means may be located within the tubing and/or at one or both of the terminal ends (first terminal end and second terminal end). Each of these three antimicrobial means for minimizing microbial migration in a direction opposite of intended flow is briefly discussed below.

Check-valves as used in this specification refer to devices which may be intended to allow fluid flow in only one direction. Check-valves may accomplish this function using a variety of means well known in the art, such as utilizing springs with balls, flaps (diaphragms), one-way gates (swing and/or tilt), duckbills, and the like. A given check-valve may generally have at least one inlet and at least one outlet, where the inlet and the outlet are generally points of connection to the check-valve. Check-valves may be in an open configuration when no back pressure is applied to the check-valve, permitting flow in the desired direction. Check-valve locations in some embodiments may be positioned at either terminal end of the tubing, both terminal ends of the tubing, or in between the two terminal ends of the tubing.

For example, a check-valve used in urinary tubing, as described and disclosed in this specification, permits urine flow in the desired direction when the upstream urine pressure exceeds the check-valve's resting state and opens the check-valve. Upstream urine pressure may be created naturally from the patient urinating, or may arise by virtue of a static head, i.e. the height of urine in tubing (and catheter) upstream of a check-valve, where the greater the height of urine, the greater the urine pressure (greater the static head of urine pressure). Such upstream urine pressure created by a static head of urine is with respect to a gravitational pull, i.e. urine like all liquid fluids flows downhill. If the exit end of urinary tubing is raised above the entry point of urinary tubing, any urine within the urinary tubing may be encouraged to flow backwards, against the intended flow, because by raising the exit end above the entry end greater downstream urine pressure has been created by a static head of urine. A check-valve in proper place (e.g., not installed backwards) within the tubing may prevent such backflow (reflux) because the check-valve may be designed to be closed when the downstream pressure exceeds the upstream pressure. In some embodiments, such a check-valve may be normally closed, only opening for normal urine flow in the direction of intended flow.

Note, the locational identifiers of "downstream" and "upstream" may be in reference to the direction of intended flow, i.e., intended flow flows from the upstream to the downstream. Such locational identifies may also be in reference to some third point in between the upstream and downstream locations, such as a check-valve.

Now turning to another antimicrobial means for minimizing microbial migration in a direction opposite of intended flow, the use of a biofilm abater within the tubing. As used in this specification, the biofilm abater is a device which may prevent or minimize biofilm movement (migration or growth) in the direction opposite of intended flow. Because biofilm movement (e.g., migration or growth) occurs more readily on wettable regions within the tubing, particularly regions which are currently wet, then the biofilm abater may be located within the tubing so as to prevent or minimize biofilm movement in the direction opposite of intended flow.

In some embodiments, biofilm abaters may circumscribe an inside diameter of the tubing. Whereas, in some embodiments, biofilm abaters may circumscribe an outside diameter of the tubing.

Biofilm abaters may operate in several ways, which are not mutually exclusive. First, the biofilm abater may inhibit microbe growth. Secondly, the biofilm abater may inhibit microbe attachment to a surface (generally a wettable surface). Inhibiting growth may involve interfering with a microbe's cellular processes, such as cellular replication or cell-wall development. While inhibiting attachment may involve creating a surface substrate that is molecularly too slippery for a microbe to attach to. Thirdly, biofilm abater may be a closed check-valve when urine is not flowing, thereby providing a physical barrier preventing biofilm from entering the catheter through the check-valve.

In some mechanisms of operation, growth inhibiting or attachment inhibiting, the biofilm abater may take on the structural and geometric properties of a ring fitted snuggly within the tubing. The biofilm abater may comprise a ring. The ring may comprise an outside diameter that may be in direct physical contact with the tubing's inside diameter, such that the tubing's inside diameter frictionally grips the ring's outside diameter. Such a ring structure may also comprise an inside diameter, configured to permit fluid flow. This point of direct physical contact between the ring and the tubing may be such that no fluid is permitted to flow between the ring's outside diameter and the tubing's inside diameter. All fluid flow may be directed through the inside diameter of the ring.

Such a ring may inhibit biofilm growth on the wettable surfaces of the ring, such as the ring's inside diameter, by the ring's wettable surfaces comprising an antimicrobial property that inhibits growth. For example, in various embodiments, the ring may be made entirely of silver (or a silver alloy) or the ring may be coated with silver (or silver alloy). Silver, in both metallic form (and alloys) and silver salt forms, is well known within the art of comprising antimicrobial properties which inhibit microbial growth and may actually kill microbes. The biofilm abater which may comprise the ring, may have a predetermined measureable length and width, wherein the ring may comprise silver or a silver coating may inhibit biofilm migration across the inside diameter of such a ring. Such a ring may be entirely constructed of metallic silver or various external surfaces of the ring may be coated with silver. Such antimicrobial properties are not limited to silver and silver coatings.

Such a ring structure may inhibit biofilm attachment to the wettable surfaces of the ring, such as the ring's inside diameter, by the ring's wettable surfaces comprising an antimicrobial property that inhibits attachment. In various embodiment, the ring's wettable surfaces, such as the ring's inside diameter may be coated with a material providing anti-attachment properties. Anti-attachment may be accomplished by forming a surface that is molecularly smooth (molecularly slippery), such that there is no molecular geometry for microbes to attach to. For example, surfaces may be treated with a Teflon® coating, which is known to result in a slippery surface that reduces microbe attachment. Other chemicals may also be used to treat surfaces yielding a molecularly smooth surface that microbes find difficult to attach to. Such coating treatments may be applied to materials of construction typical for tubing, various connectors, and check-valves, such as silicone, PVC (polyvinylchloride), PU (polyurethane), and the like.

In various embodiments, a biofilm abater may comprise a ring, which may comprise a molecularly smooth coating of the ring's wettable surfaces, which may then inhibit biofilm migration across the inside diameter of such a ring because the microbes find difficulty in attaching to such coated regions. In various embodiments, the ring's outside diameter may not be treated with the molecularly smooth coating, as such a coating may interfere with the tubing's inside diameter frictionally gripping the ring's outside diameter.

Now turning to the third antimicrobial means for minimizing microbial migration in a direction opposite of intended flow, which may be regions of the tubing which may comprise an antimicrobial coating, where such regions are predominantly wettable regions. Such coated regions of tubing may function in an equivalent manner as the biofilm abater embodiments discussed above, but instead of coating a separate component like the biofilm abater's ring, here a region or all of the tubing material of construction may be coated with one of the anti-microbial coatings. As noted above the antimicrobial coatings may either inhibit biofilm growth across the treated region or the antimicrobial coating may inhibit attachment to the coated region. Or the antimicrobial treated region may comprise both functions. For example, in various embodiments, the coated region may comprise a silver coating which may inhibit biofilm growth across the coated region. Whereas, in other embodiments, the coated region may comprise a molecularly smooth coating which may inhibit biofilm attachment to the coated region and thus inhibit biofilm migration across the coated region.

Coated regions may comprise a given length of the tubing's inside diameter, such that the coated region completely circumscribes the tubing's inside diameter for that given length, thus presenting a uniform barrier to biofilm migration (movement). Wettable treated regions may also comprise various interior surfaces of various connectors, with and without check-valves, as well as check-valves without connectors. For example, and without limiting the scope of the present invention, in various embodiments a check-valve's interior wettable surfaces may be coated with the antimicrobial coating.

In various embodiments, a coated region may comprise a region of outside diameter tubing that is immediately proximal of the first terminal end and/or of the second terminal end, as such outside diameter regions although are generally non-wettable regions, they are regions which are nevertheless prone to contaminating urinary tubing due to their close proximity and access to inside diameter wettable regions of the tubing. Such a distance of "immediately proximal" may be up to and including 8 inches from either terminal end (first terminal and/or second terminal end). In some embodiments, an entirety of the tubing may be coated with the antimicrobial material.

In some embodiments, the tubing material of construction itself, i.e., not just the surface regions, may have antimicrobial ingredients added into the materials formulation to yield a cured material that exhibits antimicrobial properties.

Each of these means for minimizing microbial migration in the direction opposite of intended flow may be located within the tubing at various locations along the tubing's length, at the tubing's first terminal end, or at the tubing's second terminal end.

In the following discussion that addresses a number of embodiments and applications of the present invention, reference is made to the accompanying figures (drawings) that form a part thereof, where depictions are made, by way of illustration, of specific embodiments in which the invention may be practiced. It is to be understood that other embodiments may be utilized and changes may be made without departing from the scope of the invention.

Figure 1A:
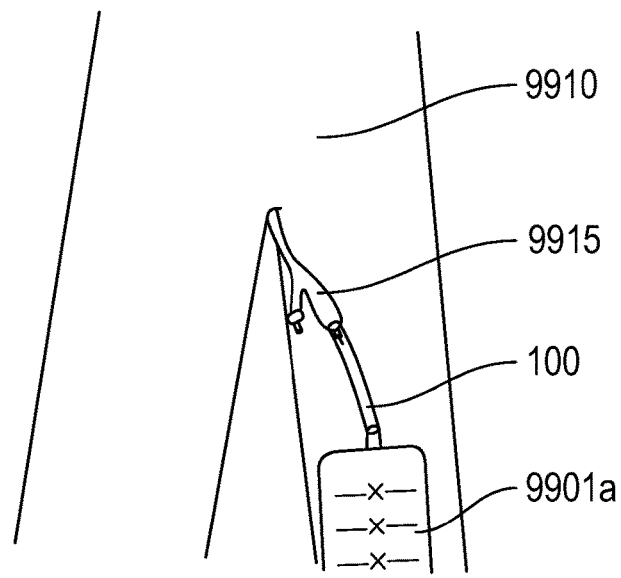
FIG. 1A depicts an embodiment of urinary tubing (hereinafter, "tubing") connected at one end to a catheter and at the other end to a urine leg bag, shown from a frontal view. The catheter is shown as connected to a patient.
Figure 1C:
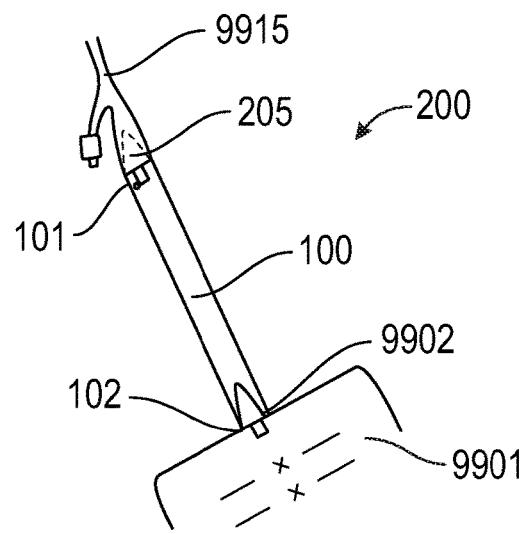
FIG. 1C depicts an embodiment of tubing connected at one end to a catheter and at the other end to a urine bag, shown from a top view.
Figure 1B:
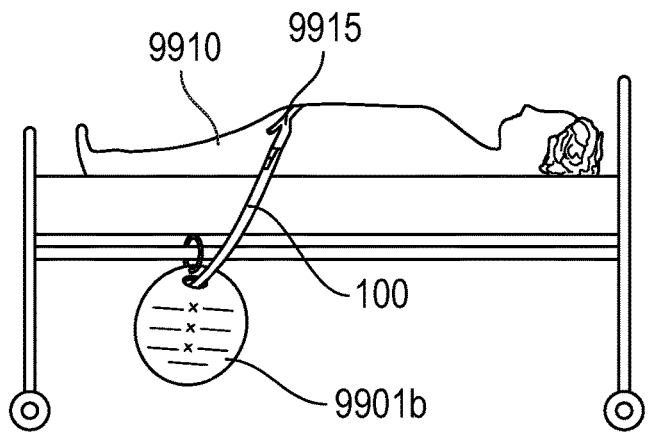
FIG. 1B depicts an embodiment of tubing connected at one end to a catheter and at the other end to a urine bed bag, shown from a longitudinal side view. Here the catheter is connected to a patient that is lying down on a bed.

The FIG. 1 series of figures includes FIG. 1A, FIG. 1B, and FIG. 1C. The FIG. 1 series of figures may serve two functions: (1) to place the tubing invention into context of being connected to a catheter at one end and a urine bag at an opposing end; and (2) to depict the inventive system, wherein the system may comprise the inventive tubing, as well as a catheter.

FIG. 1A depicts a tubing 100 connected at one end to a catheter 9915 and at the other end to a urine leg bag 9901a, shown from a frontal view. Catheter 9915 as shown may be properly connected to patient 9910, i.e., by proper partial insertion into patient 9910's urethra, i.e., catheter 9915 may be an indwelling catheter, such as a Foley catheter. FIG. 1B depicts tubing 100 connected at one end to catheter 9915 and at the other end to a urine bed bag 9901b, shown from a longitudinal side view. Here catheter 9915 may be properly connected to patient 9910 that is lying down or otherwise occupying a bed. FIG. 1C depicts an embodiment 200 of tubing 100 connected at one terminal end, a first terminal end 101 to catheter 9915, and at the other terminal end, a second terminal end 102 to urine bag 9901, shown from a top view.

Figure 2:
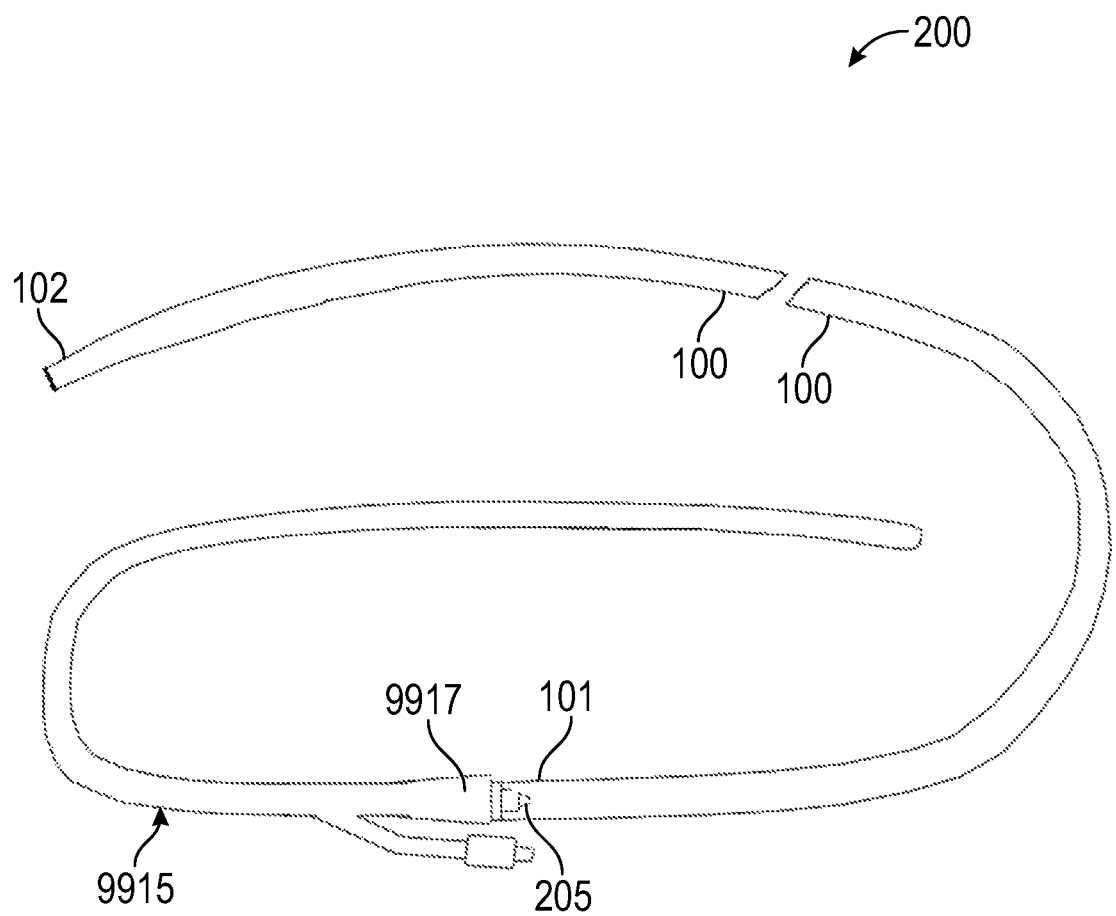
FIG. 2 depicts an embodiment of tubing comprising a connector integrated with check-valve, where one end of the tubing is connected to an exit port of a catheter via the connector integrated with check-valve, shown from a top view.

FIG. 2 depicts embodiment 200 of tubing 100 comprising a connector integrated with check-valve 205, where first terminal end 101 of tubing 100 may be connected to an exit port 9917 of catheter 9915 via connector integrated with check-valve 205, shown from a top view.

Note in FIG. 2 the entire catheter 9915 and the entire tubing 100 may be depicted; while patient 9910 and urine bag 9901 are not depicted. Whereas, in FIG. 2A, and FIG. 2B the focus may be depicting the connection where tubing 100 may be connected to catheter 9915, which may utilize connector integrated with check-valve 205 to connect exit port 9917 to first terminal end 101 of tubing 100.

In terms of tubing 100 overall length, such an overall length may be short to accommodate use with leg bag 9901a. For example, and without limiting the scope of the present invention, such an overall length of tubing 100 may be from two inches to seven inches; or longer or shorter in other embodiments. In other embodiments, overall length may be twenty-four inches or longer to accommodate use with bed bag 9901b.

Figure 2A:
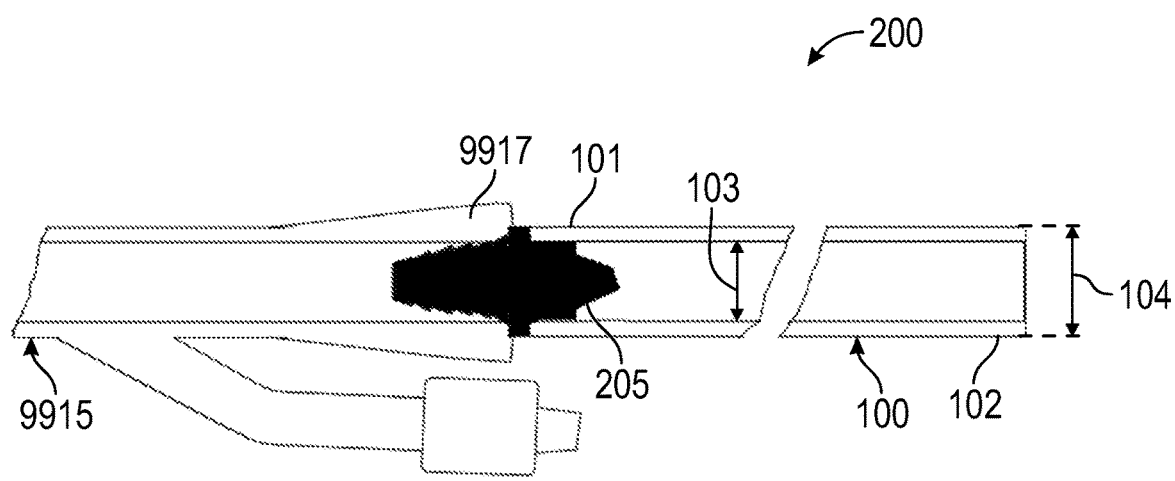
FIG. 2A depicts the embodiment of the tubing of FIG. 2, shown from a close up longitudinal cross-sectional view.
Figure 2B:
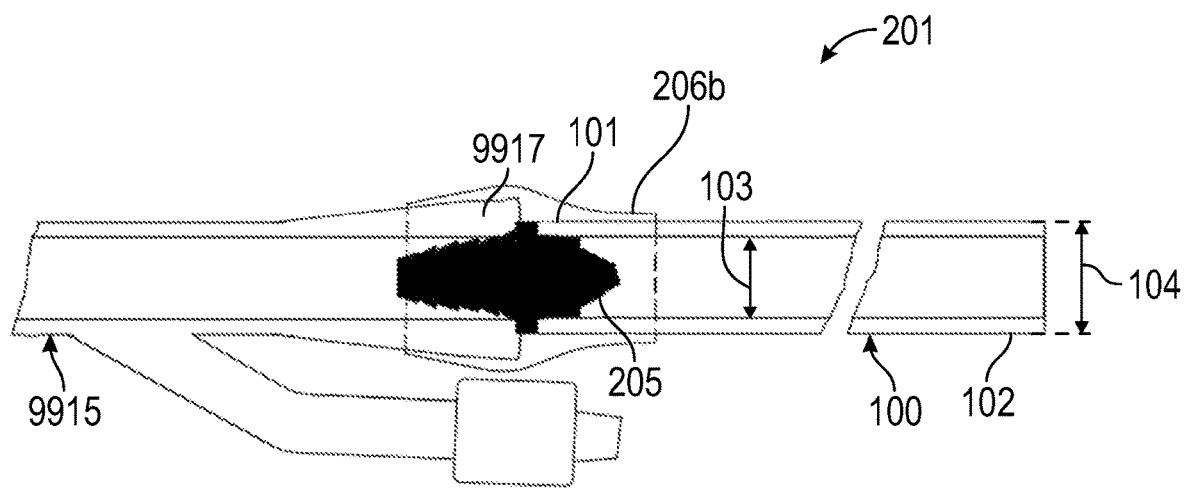
FIG. 2B depicts an embodiment of the tubing of FIG. 2A, but with an addition of tape wrapping a connection between the catheter and the tubing, shown from a longitudinal cross-sectional view.

FIG. 2A depicts embodiment 200 of tubing 100, shown from a close up longitudinal cross-sectional view of the connection. FIG. 2B depicts embodiment 201 of tubing 100 with an addition of tape 206b wrapping around the connection between catheter 9915 and tubing 100, shown from a longitudinal cross-sectional view.

First general structure which may be common to both embodiment 200 and 201 is discussed, followed by additional structure of embodiment 201. Embodiment 200 of tubing 100 may comprise: first terminal end 101, second terminal end 102, and connector integrated with check-valve 205. First terminal end 101 may longitudinally oppose second terminal 102. Connector integrated with check-valve 205 may be a single article of manufacture. Connector integrated with check-valve 205 may be located at first terminal end 101 and may be configured to connect tubing 100 to catheter 9915. The connection between catheter 9915 and tubing 100 may be formed by connecting first terminal end 101 to catheter exit port 9917 via connector with check-valve 205 (wherein that connector and check-valve are integral with respect to each other). Connector with check-valve 205 may comprise two opposing ends, where one end may be sized to frictionally and removably couple with an inside diameter of first terminal end 101 and where the other end may likewise be sized to frictionally and removably couple with an inside diameter of exit port 9917. And the check-valve component of connector integrated with check-valve 205 may be located internally within connector integrated with check-valve 205, and may prevent urine backflow (reflux), which then serves as one example of a means for minimizing microbial migration in a direction opposite of intended flow.

In various embodiments, there may be more than one connector as a component of tubing 100. Additional such connectors may or may not include a check-valve. In various embodiments, there may be other means for minimizing microbial migration in a direction opposite of intended flow. For example, there may be more than one check-valve. The means for minimizing microbial migration in the direction opposite of intended flow may be selected from one or more of the group comprising at least one check-valve (205, 308, and 605), at least one biofilm abater 613, and a region treated with an antimicrobial coating (e.g., such as region 622). The region of tubing 100 may comprise a surface which may be wetted by fluid flowing within tubing 100, such as urine flowing downstream. Such means for minimizing microbial migration in the direction opposite of intended flow may be located in tubing 100, at first terminal end 101, or at second terminal end 102. See the FIG. 6F discussion below for an embodiment including at least two check-valves (205 and 605). Biofilm abaters 613 are discussed in the FIG. 6B, FIG. 6C, and FIG. 6D discussions. And see the FIG. 6E discussion below for an embodiment including wettable region treated with an antimicrobial coating.

As depicted in FIG. 2B, embodiment 201 of tubing 100 may comprise the additional component of tape 206b. Connector integrated with check-valve 205 while connected to first terminal end 101 may comprise a length of tape 206b wrapped around the connection between the first terminal end 101 and the exit port 9917 to prevent the connection from becoming disengaged which the minimizes ingress of contaminants, such as microbes, into tubing 100. Securing the connection with tape 206b facilitates maintaining a closed-system. In various embodiments, when tape 206b has been wrapped around the connection, tape 206b may circumscribe a portion of terminal end 101 and a portion of exit port 9917.

In various embodiments, tape 206b may comprise a bonding means for tape 206b gripping outside surfaces of exit port 9917 and first terminal end 101. For example, such a bonding means may be formed by at least one side of tape 206b having an adhesive property.

Tape 206b may be a sub-category of the broader category referred to as a "coupling sleeves" 206 within this specification. That is, coupling sleeve 206 may comprise tape 206b. See the discussion of the FIG. 4 and FIG. 5 series of figures for further details regarding coupling sleeve 206.

In various embodiments, tape 206b may comprise a color on a side facing a viewer, where the purpose of such a color may be to warn a medical practitioner that terminal end 101 should not be disengaged from exit port 9917, while catheter 9915 may be inserted into patient 9910's urethra without some precaution taken to prevent opening of the closed-system. For example, and without limiting the scope of the present invention, such a color might be a bright orange, yellow, or red; and may have a written warning on the tape. Product literature and media (e.g., product inserts, white papers, website media, etc.) may include instructions as to the warning not to disengage such colored tape 206b. Tape 206b may serve at least two functions: (1) to prevent opening of an otherwise closed-system; and (2) to warn against breaching an otherwise closed-system.

Figure 3A:
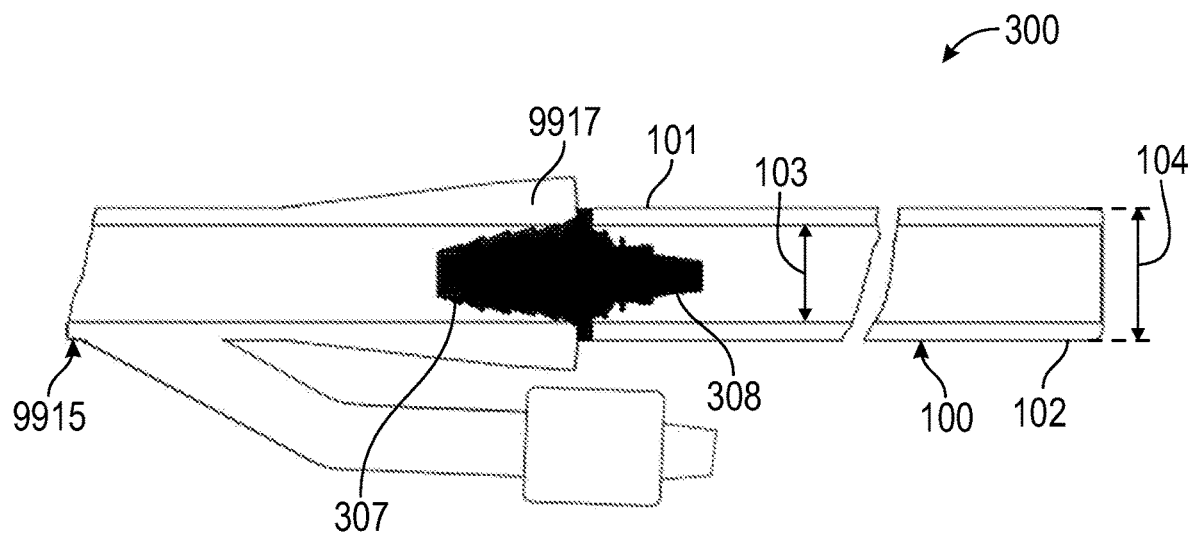
FIG. 3A depicts an embodiment of tubing which may comprise a connector with a non-integral check-valve, where one end of the tubing is connected to an exit port of a catheter via the connector with the non-integral check-valve, shown from a longitudinal cross-sectional view.

Now turning to the FIG. 3 series of figures. The FIG. 3 series of figures may be generally the same as the FIG. 2 series of figures, with the exception that connector integrated with check-valve 205 may be replaced with a connector 307 and a check-valve 308. FIG. 3A depicts embodiment 300 of tubing 100 which may comprise connector 307 coupled to non-integral check-valve 308, where first terminal end 101 of tubing 100 may be connected to exit port 9917 of catheter 9915 via connector 307, wherein connector 307 may be coupled to non-integral check-valve 308, shown from a longitudinal cross-sectional view.

In embodiment 300 (and 301), tubing 100 may comprise at least one connector 307 coupled to check-valve 308, where connector 307 and check-valve 308 may be separate articles of manufacture which may be coupled together in tubing 100. Connector 307 with coupled check-valve 308 may be connected to first terminal end 101 and may be configured to connect first terminal end 101 to exit port 9917 of catheter 9915.

In various embodiments, such a coupling of connector 307 to check-valve 308 may be permanent. Whereas, in other embodiments, such a coupling may be removable, i.e., after coupling, check-valve 308 may be disengaged from connector 307.

Various means may be used to couple connector 307 to non-integral check-valve 308. Connector 307 may frictionally hold check-valve 308. Check-valve 308 may be snapped into connector 307. Connector 307 may be solvent bonded to check-valve 308, when both components are constructed of appropriate polymers which may be solvent bonded together. Connector 307 may be ultrasonically welded to check-valve 308. Connector 307 may be glued to check-valve 308 using an appropriate adhesive (e.g., via a medical grade cyanoacrylate).

Figure 3B:
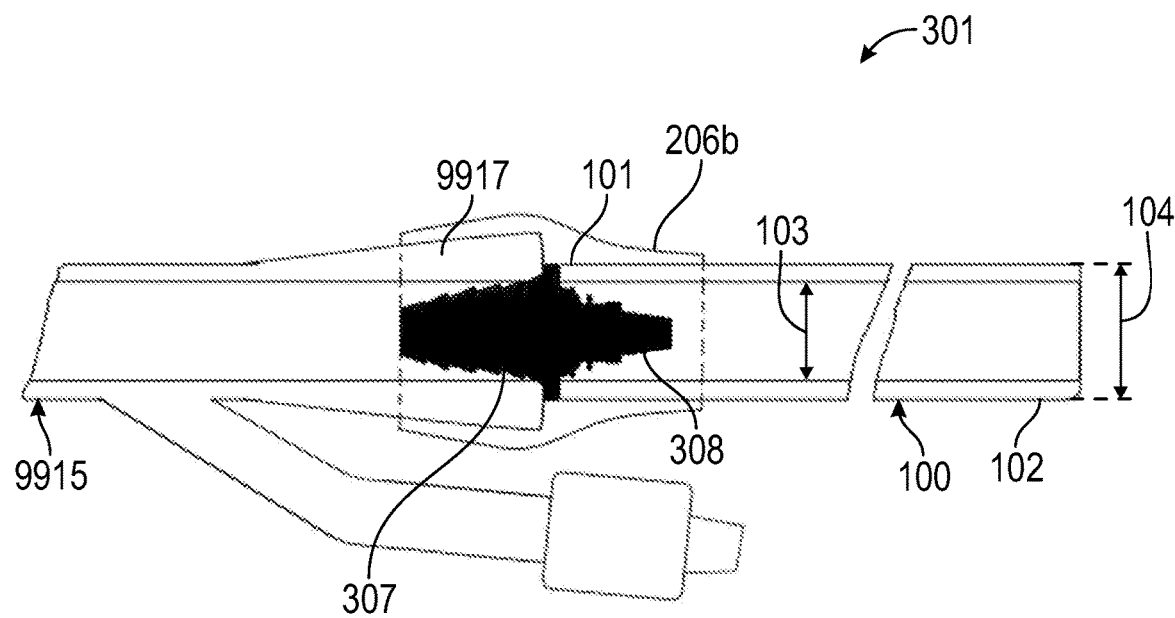
FIG. 3B depicts an embodiment of the tubing of FIG. 3A, but with an addition of tape wrapping a connection between the catheter and the tubing, shown from a longitudinal cross-sectional view.

FIG. 3B depicts a similar embodiment shown in FIG. 2B, with the inclusion of tape 206b wrapping around the connection. FIG. 3B depicts embodiment 301 of tubing 100 with an addition of tape 206b wrapping the connection between catheter 9915 and tubing 100, shown from a longitudinal cross-sectional view.

Figure 4:
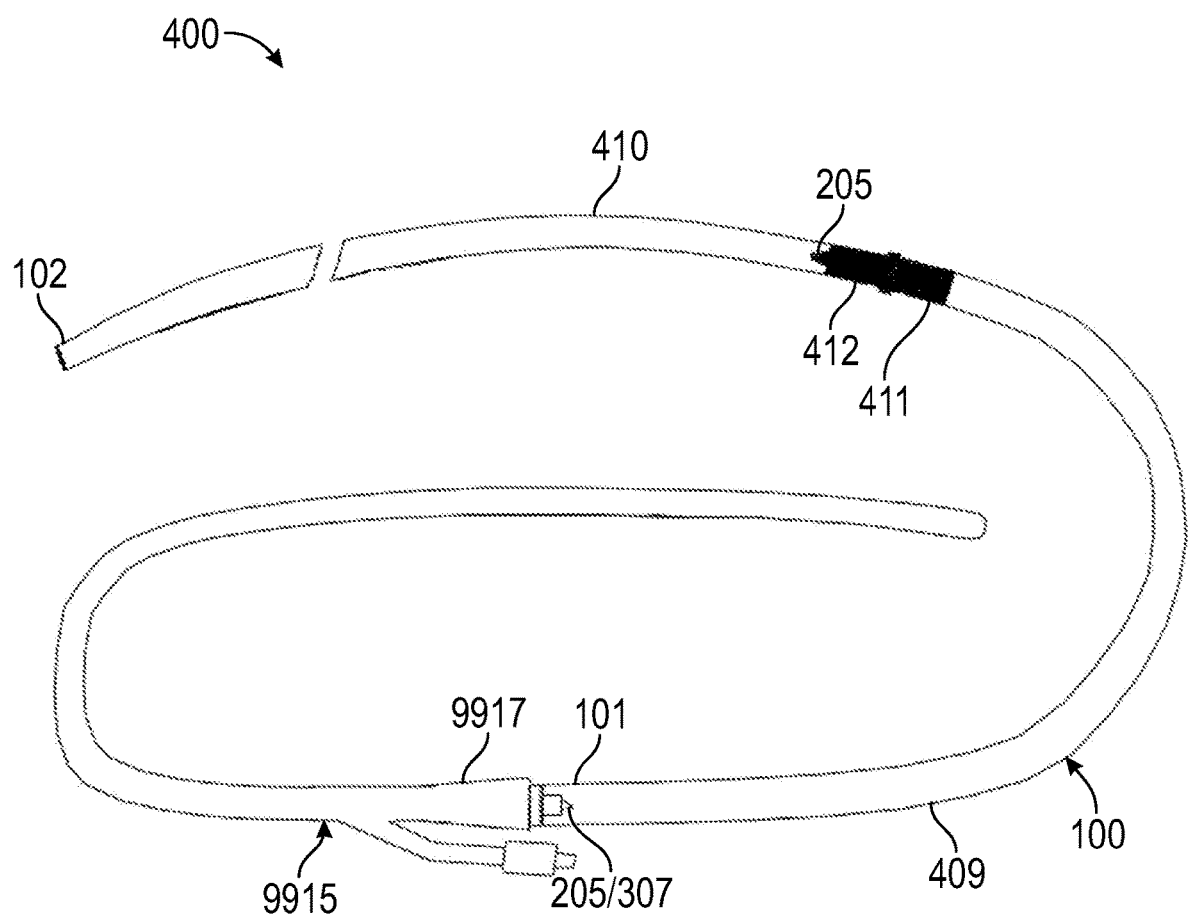
FIG. 4 depicts an embodiment of tubing, but where the tubing may be sub-divided at a joint into two smaller tubes such that a connector integrated with check-valve may be inserted between the two smaller tubes to join the two smaller tubes, which then form the tubing, shown from a top view.

The FIG. 4 and FIG. 5 series of figures may introduce tubing embodiments (400, 401, 500, and 501) where a single length of tubing 100 may be cut into two smaller pieces of tubing and then joined back together via a connector with a check-valve to form a single length of tubing 100. Such embodiments (400, 401, 500, and 501) may then provide for the means for minimizing microbial migration in a direction opposite of intended flow to be located within tubing 100; as opposed to locating the means for minimizing microbial migration in a direction opposite of intended flow at either first terminal end 101 (e.g. as shown in the FIG. 2 and FIG. 3 series of figures) and/or at second terminal end 102.

Such embodiments (400, 401, 500, and 501) may not be mutually exclusive with locating the means for minimizing microbial migration in a direction opposite of intended flow at either first terminal end 101 and/or second terminal end 102. Embodiments (400, 401, 500, and 501) may also comprise other means for minimizing microbial migration in a direction opposite of intended flow which may be located at either first terminal end 101 and/or second terminal end 102.

FIG. 4 depicts embodiment 400 of tubing 100 where tubing 100 may be sub-divided at a joint into two smaller tubes (409 and 410) such that connector integrated with check-valve 205 may be inserted between the two smaller tubes (409 and 410) to join the two smaller tubes (409 and 410), which then form a complete length of tubing 100, shown from a top view.

In embodiment 400, tubing 100 may comprise: first tube 409, second tube 410, a joint, and connector integrated with check-valve 205. First tube 409 may comprise first terminal end 101 and a third terminal end 411. First terminal end 101 longitudinally opposes third terminal end 411. Second tube 410 may comprise second terminal end 102 and a fourth terminal end 412. Second terminal end 102 may longitudinally oppose fourth terminal end 412. As noted above, first terminal end 101 may longitudinally oppose second terminal end 102. The joint may be made between first tube 409 and second tube 410 to form tubing 100 by using connector integrated with check-valve 205 to connect third terminal end 411 to fourth terminal end 412.

As used in this specification, "joint" refers to joining first tube 409 to second tube 410; while "connection" may refer to connecting tubing 100 to catheter 9915 or to connecting tubing 100 to urine bag 9901.

Figure 4A:
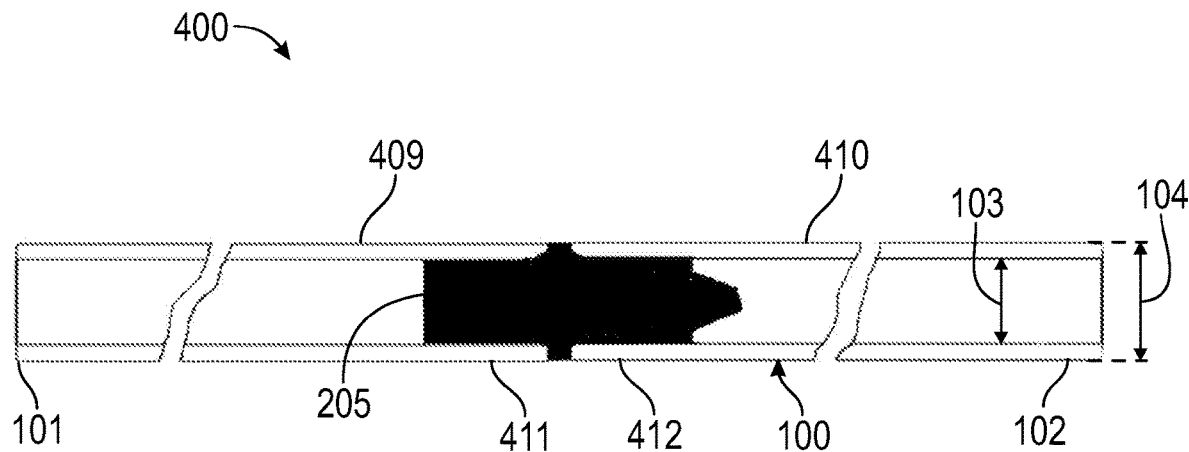
FIG. 4A depicts the embodiment of tubing of FIG. 4, shown from a longitudinal cross-sectional view.

In terms of tubing 400, the single length may be short to accommodate use with leg bag 9901a. For example, and without limiting the scope of the present invention, single length of tubing 100 may be from about two inches to seven inches. In some embodiments, the single length may be about twenty-four inches or longer to accommodate use with bed bag 9901b. In some embodiments, the single length may be less than about one inch to a desired length to accommodate attachment to various types of bags. Wherein "about" in this paragraph may be plus or minus 0.25 of an inch FIG. 4A depicts embodiment 400 of tubing 100, shown from a longitudinal cross-sectional view focusing on the joint between first tube 409 and second tube 410 that may be formed by connector integrated with check-valve 205 connecting third terminal end 411 to fourth terminal end 412.

Figure 4B:
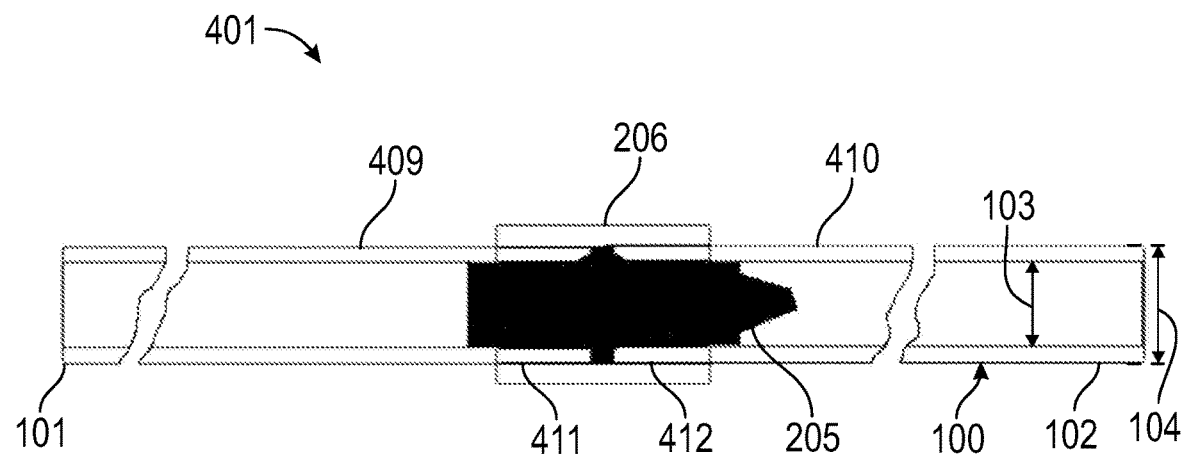
FIG. 4B depicts an embodiment of the urinary tubing of FIG. 4A, but where the joint is circumscribed by a coupling sleeve, shown from a longitudinal cross-sectional view.

FIG. 4B depicts embodiment 401 of tubing 100 where the joint may be circumscribed by coupling sleeve 206, shown from a longitudinal cross-sectional view. Tubing 100 may comprise coupling sleeve 206 which may circumscribe the joint between third terminal end 411 and fourth terminal end 412. Coupling sleeve 206 may be configured to grip the joint, such that coupling sleeve 206 translation along tubing 100 may be minimized, i.e., coupling sleeve 206 may not freely slide along the longitude of tubing 100. In some embodiments, such gripping may be accomplished by coupling sleeve 206 comprising geometry to frictionally grip tubing 100. For example, coupling sleeve 206 may comprise an inside diameter which may be sized to be substantially the same as outside diameter 104 of tubing 100, such that there may be friction between coupling sleeve 206 and tubing 100 when tubing 100 may be inserted into the inside diameter of coupling sleeve 206. In other embodiments, coupling sleeve 206 may grip the joint by the bonding means. The bonding means may be selected from one or more of the group comprising heat welding, ultrasonic welding, solvent bonding, chemical adhesives (including adhesive tape), and the like. Coupling sleeve 206 may be bonded to outside diameter 104 of tubing 100 in a region proximal to each side of the joint to prevent the joint from becoming disengaged which minimizes ingress of contaminants, such as microbes, into tubing 100.

Coupling sleeve 206 may comprise a length of tape 206b wrapped around the joint to prevent the joint from becoming disengaged which minimizes ingress of contaminants, such as microbes, into the tubing 100. Tape 206b may comprise a color, e.g., a bright color as in red, to serve as a warning to a viewer, such as a medical practitioner, that the joint should not be opened and disengaged.

Now turning to the FIG. 5 series of figures. The FIG. 5 series of figures may be generally the same as the FIG. 4 series of figures, with the exception that connector integrated with check-valve 205 may be replaced with connector 307 and check-valve 308.

Figure 5A:
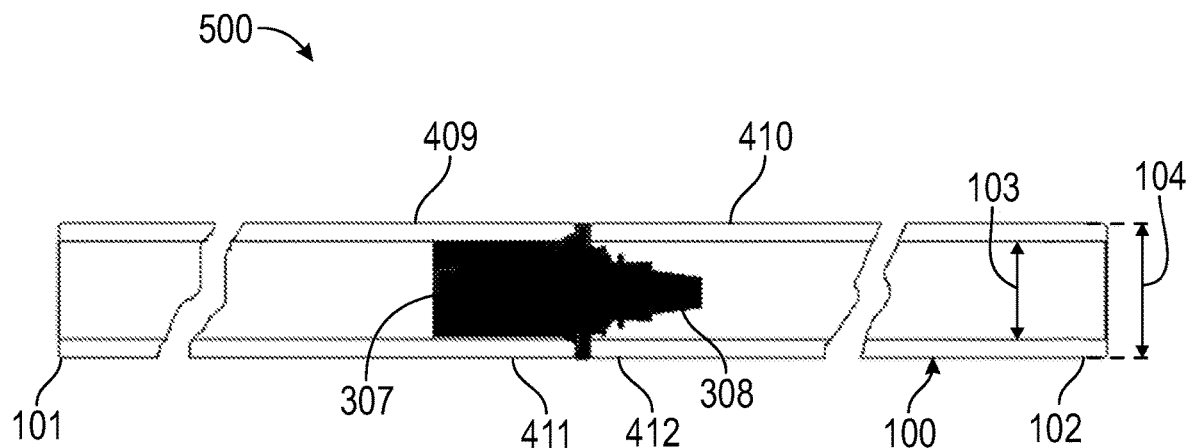
FIG. 5A depicts an embodiment of tubing, but where the tubing may be sub-divided at a joint into two smaller tubes such that a connector with non-integral check-valve may be inserted between the two smaller tubes to join the two smaller tubes, which then form the tubing, shown from a longitudinal cross-sectional view.

FIG. 5A depicts embodiment 500 of tubing 100 where tubing 100 may be sub-divided at the joint into two smaller tubes (409 and 410) such that connector 307 with non-integral check-valve 308 may be inserted between the two smaller tubes (409 and 410) to join the two smaller tubes (409 and 410), which then may form tubing 100, shown from a longitudinal cross-sectional view.

Figure 5B:
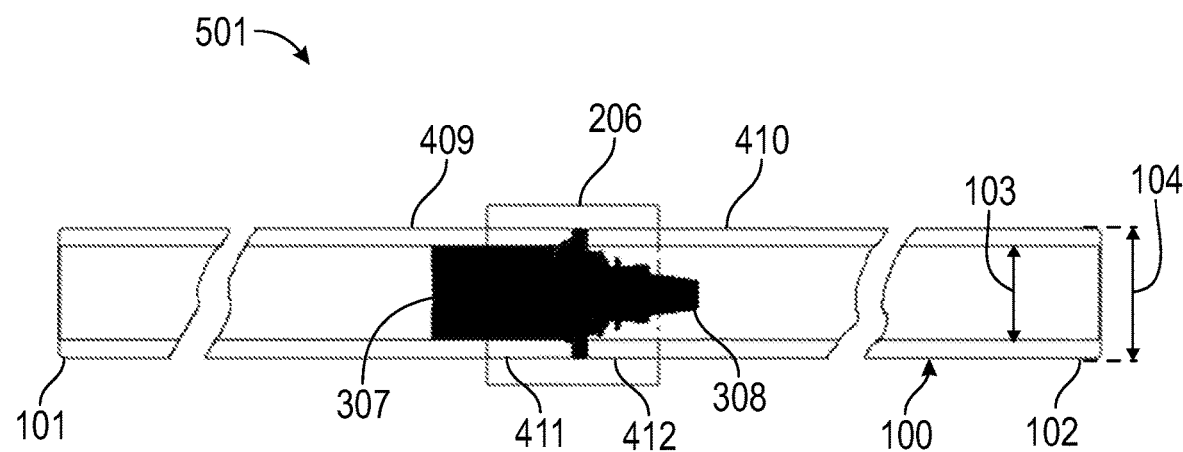
FIG. 5B depicts an embodiment of the urinary tubing of FIG. 5A, but where the joint is circumscribed by a coupling sleeve, shown from a longitudinal cross-sectional view.

The details regarding the coupling of connector 307 to check-valve 308 were first discussed above under the FIG. 3A discussion and that discussion may apply here for embodiment 500 depicted in FIG. 5A and of embodiment 501 depicted in FIG. 5B.

FIG. 5B depicts embodiment 501 of tubing 100 of FIG. 5A, where the joint may be circumscribed by coupling sleeve 206, shown from a longitudinal cross-sectional view. The details regarding coupling sleeve 206 were discussed above under the FIG. 4B discussion and that discussion may apply here for embodiment 501.

Now turning to the FIG. 6 series of tubing 100 embodiments. The FIG. 6 series of figures addresses at least seven distinct embodiments, which may be combined into various embodiments, also within the scope of the present invention.

Figure 6A:
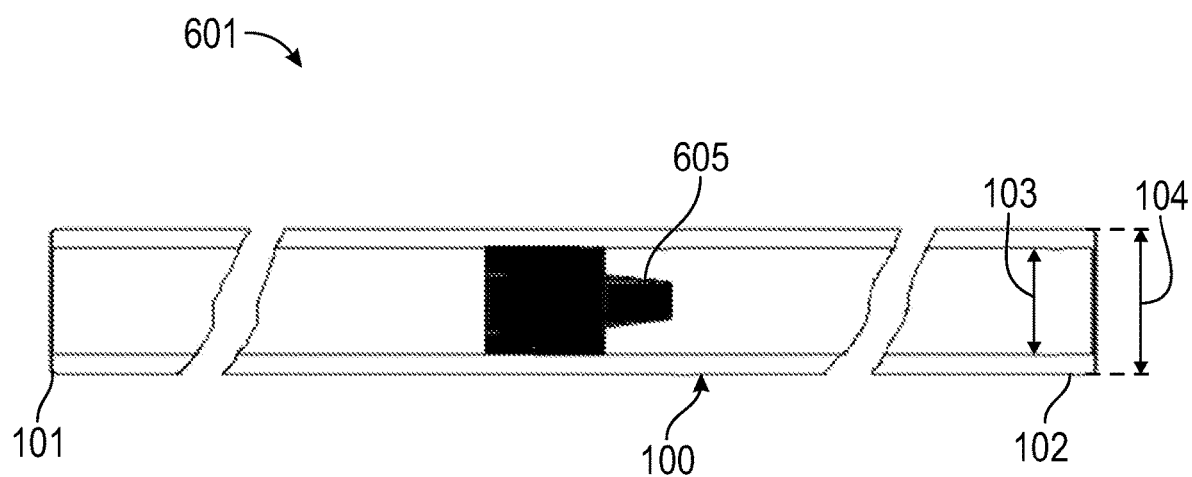
FIG. 6A depicts an embodiment of tubing where a check-valve may have been inserted into the tubing by pushing the check-valve into a desired location, shown from a longitudinal cross-sectional view.

FIG. 6A depicts embodiment 601 of tubing 100 where check-valve 605 may have been inserted into tubing 100 by pushing the check-valve into a desired location, shown from a longitudinal cross-sectional view.

In embodiment 601, tubing 100 may comprise check-valve 605. Check-valve 605 may be assembled into tubing 100 by pushing check-valve 605 inside tubing 100 to a desired location along a length of tubing 100 such that tubing 100 may frictionally grip check-valve 605 to maintain the desired location, while also forming a complete seal between a periphery of check-valve 605 (e.g., an outside diameter of check-valve 605) and inside of tubing 100 (e.g., an inside diameter 103 of tubing 100) where the check-valve 605 may be positioned. Check-valve 605 may comprise an outside diameter, as part of check-valve 605's periphery, which may be substantially similar to inside diameter 103 of tubing 100, such that check-valve 605 may not translate (slide) within tubing 100 unless a force may be applied to overcome the frictional gripping force. The nature of such frictional gripping may be to form a seal between the outside diameter of check-valve 605 with inside diameter 103 of tubing 100, such that fluid flowing through tubing 100 may not pass between the outside diameter of check-valve 605 and inside diameter 103 of tubing 100. Such a complete seal may also be formed with the aid of one or more o-rings (or gaskets) circumscribing outside diameter of check-valve 605.

In various embodiments, tubing 100 may first be heated to increase its pliability and to expand tubing 100, then subsequently check-valve 605 may be pushed inside tubing 100 to the desired location. Upon tubing 100 cooling, tubing 100 may contract and increase frictional gripping between tubing 100 and check-valve 605.

In some embodiments, check-valve 605 may also be positionally fixed within tubing 100 by ultrasonically welding, solvent bonding, and by use of chemical adhesives.

While only one check-valve 605 may be depicted in FIG. 6A, such a method of positioning check-valves within tubing 100 may be used to place a plurality of check-valves (such as check-valve 605) within tubing 100.

Notes regarding check-valve 605 and check-valve 308: Check-valve 308 may refer to a check-valve that may be configured to couple with connector 307. Check-valve 605 may not necessarily include such a further limitation.

Figure 6B:
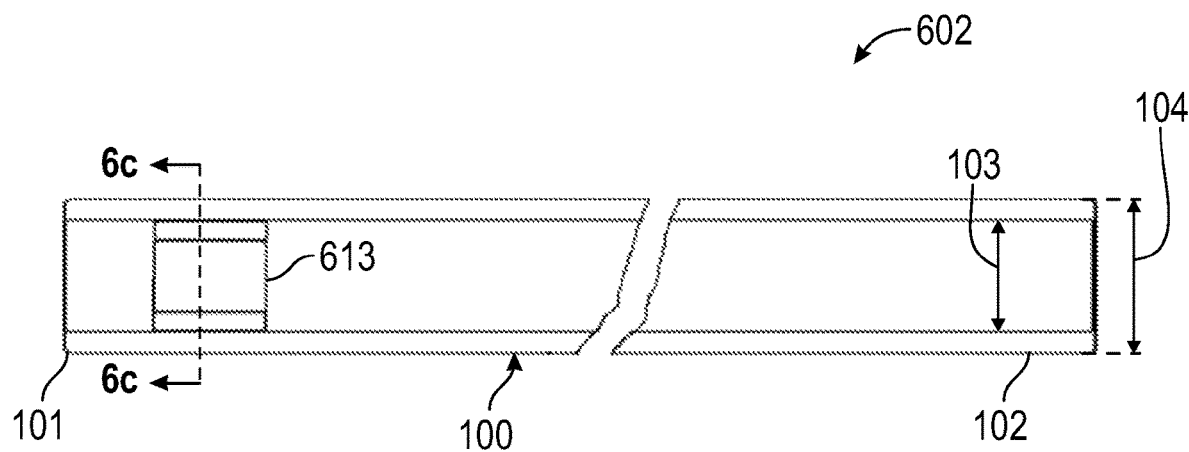
FIG. 6B depicts an embodiment of tubing with a biofilm abater inserted into the tubing, shown from a longitudinal cross-sectional view.
Figure 6C:
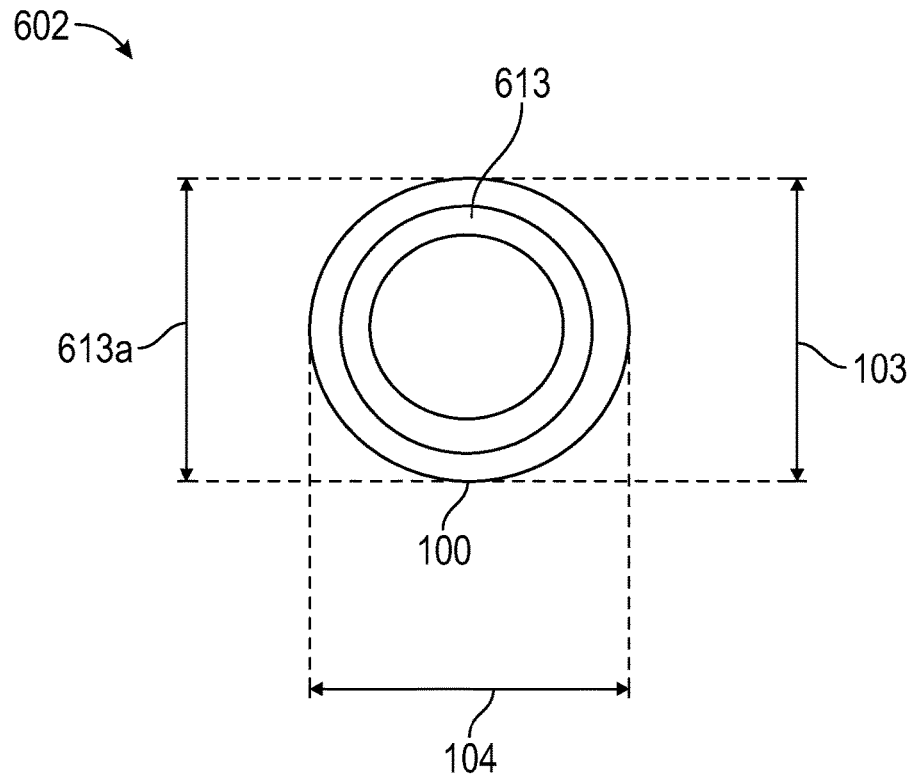
FIG. 6C depicts an embodiment of tubing with a biofilm abater inserted into the tubing, shown from a top cross-sectional view.
Figure 6D:
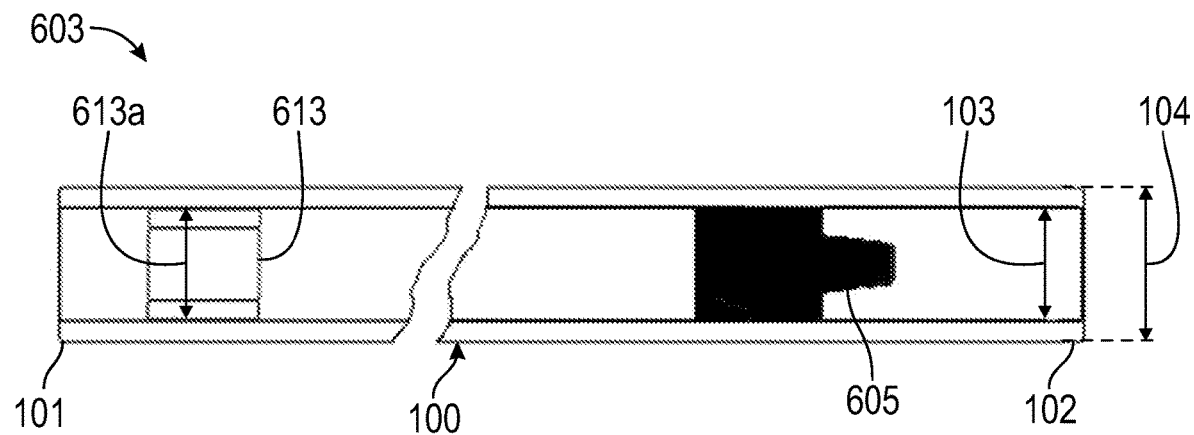
FIG. 6D depicts an embodiment of tubing with a check-valve and with a biofilm abater inserted into the tubing (upstream of) the check-valve, shown from a longitudinal cross-sectional view.

FIG. 6B, FIG. 6C, and FIG. 6D address embodiments where tubing 100 may comprise one or more biofilm abaters 613, which may reside within tubing 100.

FIG. 6B depicts embodiment 602 of tubing 100 with biofilm abater 613 inserted into tubing 100, shown from a longitudinal cross-sectional view. FIG. 6C depicts the embodiment of FIG. 6B, but shown from a top cross-sectional view.

In embodiment 602, tubing 100 may comprise one or more biofilm abater 613. Each biofilm abater 613 may comprise a ring. The ring may have structure which comprises an inside diameter, outside diameter 613a, and a thickness which may be defined by the difference between outside diameter 613a and the inside diameter. Outside diameter 613a may be configured to fit within inside diameter 103 of tubing 100. Outside diameter 613a may be frictionally held in place in a desired location within inside diameter 103 of tubing 100. Such frictional gripping may be accomplished by outside diameter 613a being substantially similar, in terms of dimension, to inside diameter 103 of tubing 100. The ring of biofilm abater 613 may be in a desired conformation within tubing 100, such that a plane of outside diameter 613a may be perpendicular to a longitude of the tubing 100. The ring of biofilm abater 613 may comprise a longitude, wherein the longitude of the ring of biofilm abater 613 may be parallel to the longitude of tubing 100. The longitude of tubing 100 may include a length, and the longitude of the ring of biofilm abater 613 may also include a length, wherein the length of tubing 100 may be greater than the length of the ring of biofilm abater 613.

The ring of biofilm abater 613 may include surface areas covering the external surfaces of the ring. The ring of biofilm abater 613 may comprise an antimicrobial coating, covering surface areas of the ring. In various embodiments, the wettable surface areas of the ring of biofilm abater 613 may be coated with the antimicrobial coating. Outside diameter 613*a* may not be coated with the antimicrobial coating. In some embodiments, biofilm abater 613 may butt against a connector and/or check-valve.

As noted above in the general discussion of biofilm abaters preceding the figures discussion, such an antimicrobial coating may prevent microbial biofilms from growing across the surface areas of the ring which have treated with such an antimicrobial coating by inhibiting microbial growth or by inhibiting microbial attachment. For example, and without limiting the scope of the present invention, such an antimicrobial coating may comprise silver (or a silver alloy) to inhibit growth. Antimicrobial properties may be achieved where the entire ring of biofilm abater 613 may be constructed of silver, a silver alloy, or another abating material. In other embodiments, such an antimicrobial coating may comprise a molecularly smooth chemical coating yielding a molecularly smooth surface which may reduce the ability of microbes to attached to the coated region.

FIG. 6D depicts embodiment 603 of tubing 100 with check-valve 605 and with bio-film abater 613 inserted into tubing 100 upstream of check-valve 605, shown from a longitudinal cross-sectional view. FIG. 6D in comparison to FIG. 6B and FIG. 6C, includes an additional component of check-valve 605. The reason for such a spatial relationship may be as follows: an intended function of check-valve 605 may be to prevent urine backflow (reflux) which may then prevent microbes free floating and/or in suspension in urine from travelling towards patient 9910 using tubing 100 as a conduit; however, such a check-valve may not prevent biofilm growth migration (movement) towards patient 9901; and so biofilm abater 613 may be installed upstream of check-valve 605 to abate biofilm migration.

In other embodiments, such check-valves (e.g., 205, 307, and 605) may comprise both the backflow prevention function and biofilm migration prevent function by the check-valve having its wettable surfaces coated with the antimicrobial coating or means to be closed when urine is not flowing through the check valve.

Figure 6E:
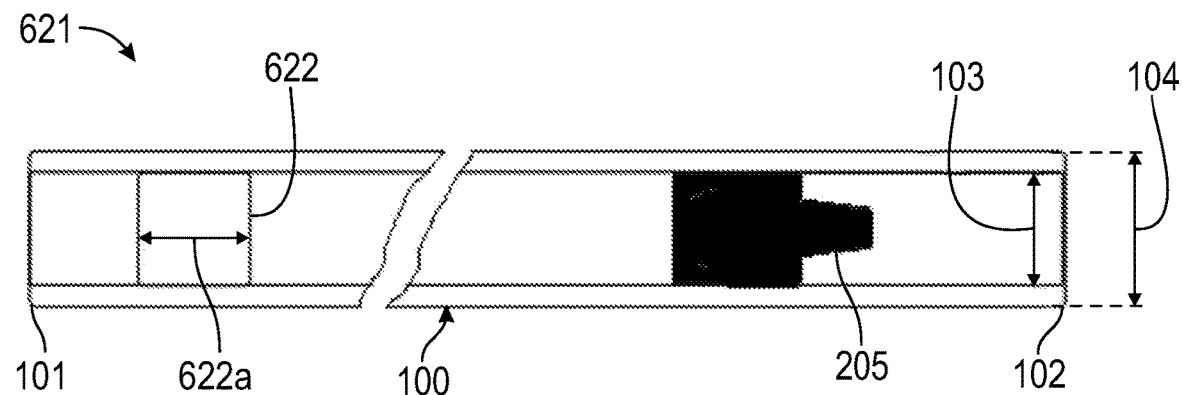
FIG. 6E depicts an embodiment of tubing where an inner region of the tubing has an antimicrobial coating, and where the coated inner region is upstream of a check-valve, shown from a longitudinal cross-sectional view.

FIG. 6E depicts embodiment 621 of tubing 100 where inside surface region 622 of tubing 100 may comprise the antimicrobial coating, and where inside surface region 622 may be upstream of check-valve 605, shown from a longitudinal cross-sectional view. Embodiment 621 depicted in FIG. 6E may be similar to embodiment 603 depicted in FIG. 6D, except here in FIG. 6E biofilm abater 613 may be replaced with inside surface region 622.

Inside surface region 622 may be a region of antimicrobial coating. Inside surface region 622 may be an example of the wetted region treated with the antimicrobial coating. As a wetted region treated with the antimicrobial coating, there may be a reduced likelihood of a microbial biofilm migrating across the wetted region treated with the antimicrobial coating. Inside surface region 622 may comprise geometry of circumscribing inside diameter 103 of tubing 100 for a sub-length 622*a* that may be less than a total length of the tubing 100. In some embodiments, sub-length 622*a* may be a substantially similar length as the total length of the tubing 100. Inside surface region 622 may be located upstream of check-valve 605.

In various embodiments, the wetted region treated with the antimicrobial coating may be selected from one or more of the group comprising at least one connector (e.g., 307), at least one check-valve (e.g., 205, 308, and/or 605), at least one biofilm abater 613, and/or inside surface region 622 of tubing 100. For example, and without limiting the scope of the present invention, any of the check-valves (205, 308, 605) depicted in the various figures may have been treated with the antimicrobial coating, particularly on the wettable surfaces. Likewise, any of the connectors (205 and 307) depicted in the various figures may have been treated with the antimicrobial coating, particularly on the wettable surfaces.

Note while more than one connector with or without check-valve, check-valve with or without connector, biofilm abater 613, and inside surface region 622 may be employed in various embodiments, there is a practical limitation to the number of such components which may be employed in any given embodiment. Such a numerical limitation arises in part because tubing 100 in any given application must have a finite total length, which is generally the length necessary to run from catheter 9915 to urine bag 9901, including some length for slack and ease of patient 9910 movement. Such a numerical limitation may arise in the case of check-valves because each additional check-valve may increase the necessary fluid pressure to flow through all check-valves installed in serial fashion and the fluid pressure itself may a maximum pressure created by patient 9910 urinating and/or by any static head of urine within catheter 9915 and tubing 100. As the number of check-valves increases the greater the required pressure is needed to flow through a serial installment of check-valves.

Figure 6F:
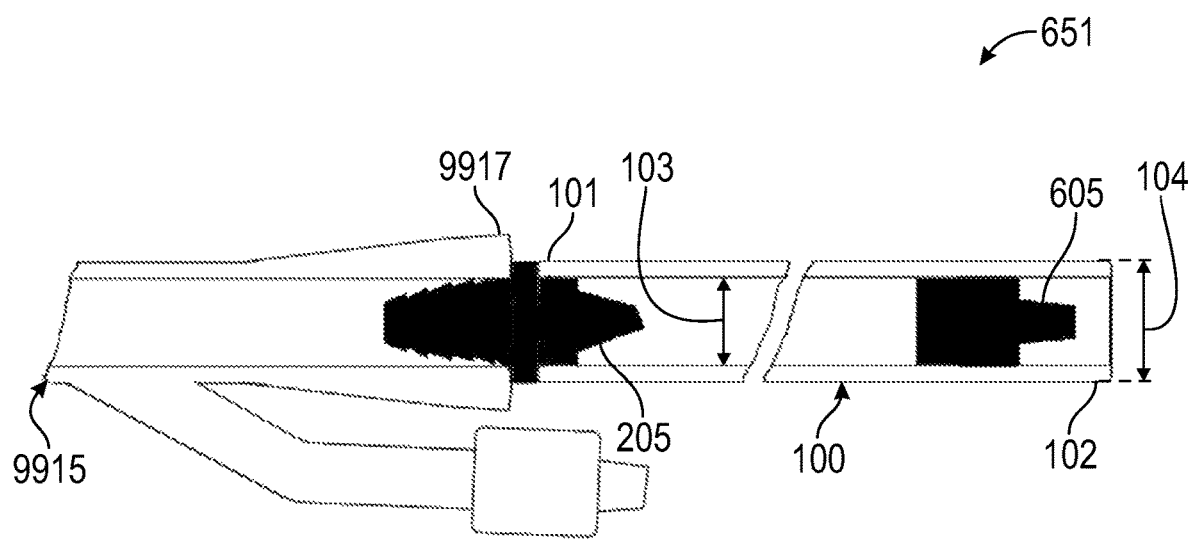
FIG. 6F depicts an embodiment of tubing where there are two check-valves inserted into the tubing, in serial fashion, shown from a longitudinal cross-sectional view.

FIG. 6F depicts embodiment 651 of tubing 100 where there are two check-valves (205 and 605) inserted into tubing 100, in serial fashion (i.e., one upstream and one downstream with respect to each other), shown from a longitudinal cross-sectional view. Connector integrated with check-valve 205 may be used to connect first terminal end 101 to exit port 9917 of catheter 9915. Check-valve 605 may be inserted and pushed into the desired location within tubing 100. In various embodiments, either one or both check-valves may also comprise the antimicrobial coating, particularly on wettable surfaces.

Figure 6G:
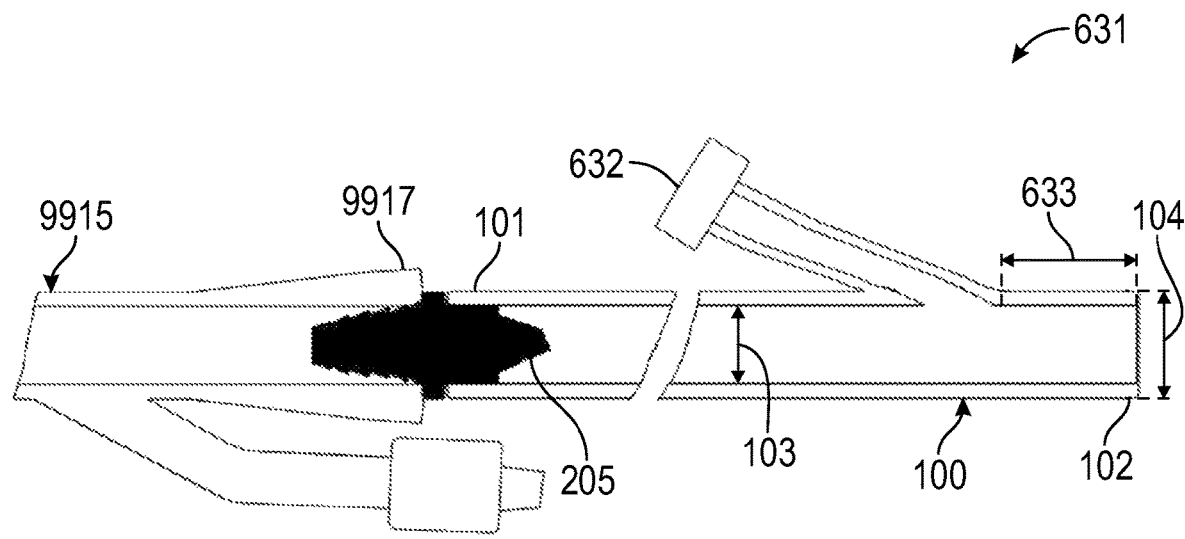
FIG. 6G depicts an embodiment of tubing which may comprise a sampling port, shown from a longitudinal cross-sectional view.

FIG. 6G depicts embodiment 631 of tubing 100 which may comprise sampling port 632, shown from a longitudinal cross-sectional view. In embodiment 631, tubing 100 may comprise sampling port 632. Sampling port 632 may be located a linear distance 633 from second terminal end 102. Sampling port 632 may be configured to receive a syringe for the purpose of a taking a sample of fluid from within tubing 100. For example, and without limiting the scope of the present invention, a medical practitioner might take a urine sample from sampling port 632 in order to determine the microbial load present within the urine or for various other purposes.

In various embodiments, sampling port 632 may be located closer to second terminal 102 than to first terminal end 101. Linear distance 633 may be 0.25 to 7.00 inches in some embodiments and other distances in other embodiments. Such a location may serve two purposes. First by placing sampling port 632 closer to second terminal end 102 (and farther from first terminal end 101), there may be less interference with patient 9910's comfort when urine samples are withdrawn from tubing 100, as movement of tubing 100 at the second terminal end 102 may be less likely to be communicated up tubing 100 to catheter 9915. Secondly, taking urine samples from tubing 100 may constitute a technical, albeit intermittent, breach of what may have otherwise been a closed-system. Withdrawing urine samples from tubing 100 may increase the likelihood of introducing unwanted contaminants, such as microbes, into tubing 100. Placing sampling port 632 farther away from catheter 9915 and patient 9910, there may be a greater likelihood of minimizing any such contaminant reaching catheter 9915 or patient 9910.

Figure 6H:
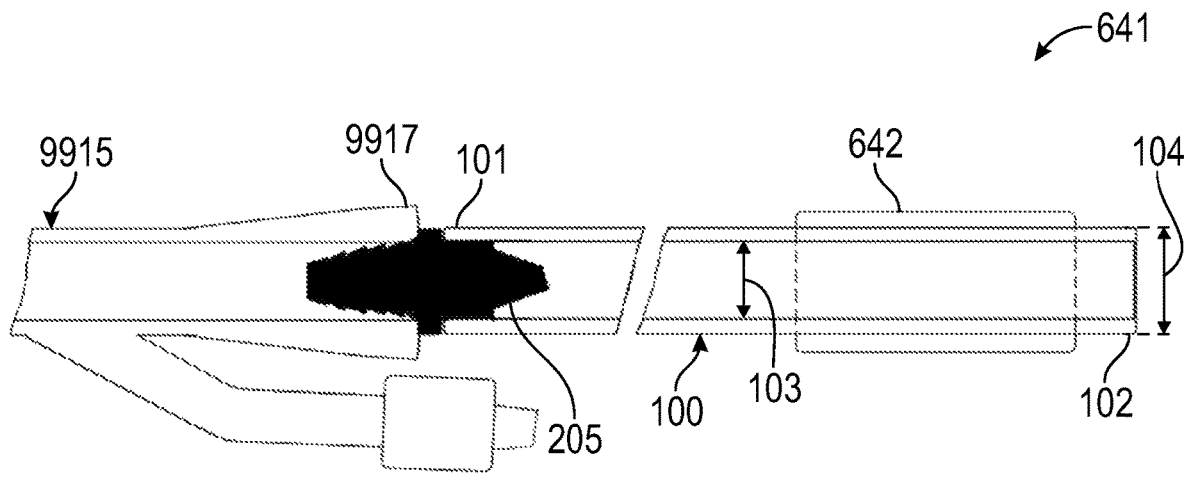
FIG. 6H depicts an embodiment of tubing which may comprise a graphical indicator which may indicate which end of the tubing may be detached from a urine bag, shown from a longitudinal cross-sectional view.

FIG. 6H depicts embodiment 641 of tubing 100 which may comprise a graphical indicator 642, which may indicate which end of tubing 100 may be detached from urine bag 9901, shown from a longitudinal cross-sectional view. Second terminal end 102 may comprise graphical indicator 642 to indicate which end of tubing 100 may be removably coupled to urine bag 9901. In various embodiments, graphical indicator 642 may be located a proximal distance from the connection of second terminal end 102 and urine bag 9901, such as from 0.125 to 7.000 inches from this connection, i.e. graphical indicator 642 may be located relatively close to this connection. In other embodiments, different dimensions for the proximal distance may be employed. Second terminal end 102 may be defined by a region which encompasses this connection and graphical indicator 642. Graphical indicator 642 may be located closer to this connection than to first terminal end 101.

In various embodiments, graphical indicator 642 may comprise tape, such as an adhesive tape, which may be wrapped around tubing 100 in the vicinity of second terminal end 102. In such embodiments, the tape does not necessarily have to wrap the connection itself, as the intent of such tape may not be to prevent disengagement of the connection, but rather to indicate that such an end may be appropriately and safely disengaged and still maintain a closed-system.

In various embodiments, graphical indicator 642 may be a color whereby such a color choice may indicate to a viewer, such as a medical practitioner, that this end of tubing 100 may be opened and disengaged from urine bag 9901, as long as proper steps are taken to minimize ingress of contaminants, such as microbes, into tubing 100. For example, and without limiting the scope of the present invention, such a color might be green. Such a color choice may also be explained in various product literature, such as product inserts and media which may be found online instructing proper use of tubing 100.

Having discussed and disclosed the inventive tubing in its various embodiments, this disclosure now turns to discussing the inventive systems which may comprise the inventive tubing as discussed above.

A system for forming and maintaining a closed-system with respect to tubing 100 connected to catheter 9915 may comprise: tubing 100, a second connector (e.g., 307 or 205), and catheter 9915. The entirety of componentry as depicted in FIG. 4 may depict such a system.

Tubing 100 may comprise: first terminal end 101, second terminal end 102, first tube 409, second tube 410, and a first connector with check-valve (e.g., 205 or 307 coupled with 308). First tube 409 may comprise first terminal end 101 and third terminal end 411. First terminal end 101 may longitudinally oppose third terminal end 411. Second tube 410 may comprise second terminal end 102 and fourth terminal end 412. Second terminal end 102 may longitudinally opposes fourth terminal end 412. The first connector may comprise a check-valve. Such a check-valve may either be connector integrated with check-valve 205 or connector 307 that has been coupled to check-valve 308. The first connector with check-valve may be used to connect third terminal end 411 to fourth terminal end 412, forming a joint between third terminal end 411 and fourth terminal end 412. First terminal end 101 may longitudinally oppose second terminal end 102.

In some embodiments, tubing 100 of the system may comprise coupling sleeve 206. Coupling sleeve 206 may circumscribe the joint. Coupling sleeve 206 may be configured to prevent third terminal end 411 from becoming disengaged from fourth terminal end 412. As noted above, coupling sleeve 206 may grip the joint (exterior of the joint) by the bonding means. Coupling sleeve 206 may comprise tape 206b. Tape 206b may be an adhesive tape. Tape 206b may be a bright color, such as red.

Catheter 9915 may comprise exit port 9917. A second connector may be used to connect first terminal end 101 to exit port 9917 such that second terminal end 102 remains available to removably couple to urine bag 9901.

The second connector may or may not comprise a check-valve. When the second connector has no check-valve, the second connector may be connector 307. When the second connector comprises a check-valve, the second connector may be connector integrated with check-valve 205 or the second connector may be connector 307 coupled to check-valve 308.

In various embodiments the various check-valves of the system may or may not comprise the antimicrobial coating. In various embodiments the system may comprise one or more biofilm abaters 613 located within tubing 100, and generally with at least one biofilm abater 613 located upstream of the first connector with check-valve. In various embodiments, the system may also comprise one or more inside surface region 622's, and generally with at least one inside surface region 622 located upstream of the first connector with check-valve. In various embodiments, the system may also comprise urine bag 9901.

When urine bag 9901 may be removed from second terminal end 102, the system may still be deemed closed from upstream of the first connector with check-valve that may be located within tubing 100; while open from downstream of the first connector with check-valve. In order to maintain the system closed from near second terminal end 102, when urine bag 9901 may be removed, additional componentry (e.g., a clamp or a cap) and various methods may be employed to close second terminal end 102.

Having discussed and disclosed various inventive tubing embodiments and inventive systems, this disclosure now turns to various methods for forming and maintaining a closed-system with respect to tubing 100 connected to catheter 9915.

A method for forming and maintaining a closed-system with respect to tubing 100 connected to catheter 9915 may comprise the steps:

Step 1: Cutting a segment of urinary tubing 100 for a purpose of connecting the segment of urinary tubing 100 to catheter 9915 and to a urine bag 9901.

Step 2: Forming a first connection between the segment of urinary tubing 100 and catheter 9915 by connecting first terminal end 101 of the segment of urinary tubing to exit port 9917 of catheter 9915 using a first connector. (Note, the first connector here in methods context is not the first connector discussed above in the systems discussion; rather the first connector here in the methods context is more akin to the second connector of systems discussion.)

Step 3: Wrapping the first connection with a first piece of tape 206b to prevent the first connection from becoming disengaged which minimizes ingress of contaminants, such as microbes, into the closed-system. This step may be optional, yet the step may be important.

Second terminal end 102 of the segment of urinary tubing 100 may be available for connection to urine bag 9901. Second terminal end 102 of the segment of urinary tubing 100 may be removably connected to urine bag 9901. Also with respect to Step 3, as discussed above, tape 206b may be colored, such as red, to indicate to a viewer to not disengage first terminal end 101 from exit port 9917 unless it may be time for catheter removal or other steps are taken to maintain the system as closed.

In various embodiments there may an additional step which precedes Step 2, wherein before making the first connection, exit port 9917, first terminal end 101, and the first connector are sterilized by treating each component with a sterilizing material. Such treating may be immersing the component within the sterilizing material. Or treating may be wiping the component down with the sterilizing material. The sterilizing material may comprise a liquid, foam, or towel wetted with the liquid or foam. The liquid or the foam may be various alcohols (e.g., isopropyl), bleach, peroxides, betadine, and the like.

The first connector may comprise a check-valve. The first connector may either comprise a check-valve such that the first connector and the check-valve are integral being a single article of manufacture, i.e., first connector may be connector integrated with check-valve 205. Or, the first connector may comprise a non-integral check-valve which is coupled to the first connector, i.e., first connector may be connector 307 coupled to check-valve 308.

The method for forming and maintaining a closed-system with respect to tubing 100 connected to catheter 9915 may comprise the following additional steps:

Step A: Cutting the segment of urinary tubing 100 into first tube 409 and second tube 410. First tube 409 may comprise first terminal end 101 and third terminal end 411. First terminal end 101 may longitudinally oppose third terminal end 411. Second tube 410 may comprise second terminal end 102 and fourth terminal end 412. Second terminal end 102 may longitudinally oppose fourth terminal end 412.

Step B: Forming a second connection between first tube 409 and second tube 410 by using a second connector to connect third terminal end 411 to fourth terminal end 412. (Note, the second connector here in methods context is not the second connector discussed above in the systems discussion; rather the second connector here in the methods context is more akin to the first connector of systems discussion.)

In various embodiments, Step A and Step B may proceed Step 2. In various embodiments, before making the second connection in Step B, third terminal end 411, fourth terminal end 412, and the second connector may be sterilized by treating each of the components with the sterilizing material.

In various embodiments, the second connection may comprise the step of securing the second connection with coupling sleeve 206. Coupling sleeve 206 may circumscribe the joint between third terminal end 411 and fourth terminal end 412. Coupling sleeve 206 may be configured to prevent third terminal end 411 from becoming disengaged from fourth terminal end 412 which may minimize ingress of contaminants, such as microbes, into the closed-system.

The step of securing coupling sleeve 206 to the joint may involve wrapping tape 206b around the joint, i.e., coupling sleeve 206 may comprise tape 206b, which may be an adhesive tape. Tape 206b may be colored, such as red, to indicate to a viewer that the second connection should not be opened unless intended to open the system.

Alternatively, the step of securing coupling sleeve 206 to the joint may involve the step of bonding coupling sleeve 206 to outside diameter 104 of tubing 100 in a region proximal to each side of the joint to prevent the second connection from becoming disengaged. Such bonding may be accomplished by the bonding means, e.g., of ultrasonic welding, solvent bonding, use of chemical adhesives, and the like.

The second connector may comprise a check-valve. The second connector may either comprise a check-valve such that the second connector and the check-valve are integral being a single article of manufacture, i.e., second connector may be connector integrated with check-valve 205. Or, the second connector may comprise a non-integral check-valve which may be coupled to the second connector, i.e., the second connector may be connector 307 coupled to check-valve 308.

The method for forming and maintaining a closed-system with respect to tubing 100 connected to catheter 9915 may comprise the following additional steps:

Step 4: Attach graphical indicator 642 to outside diameter of tubing 104 at the proximal distance from second terminal end 102. See FIG. 6H and the above discussion of graphical indicator 642. In some embodiments, graphical indicator 642 may be green colored adhesive tape. In some embodiments, Step 4 may be optional.

Step 5: When urine bag 9901 may be changed by removing urine bag 9901 and replacing urine bag 9901 with a new urine bag, the segment of urinary tubing 100 may be clamped shut with a clamp prior to removal of urine bag 9901. The clamp may remain in place until the new urine bag may be attached to second terminal end 102 at which point the clamp may be removed. It may be desirable to clamp shut tubing 100 as near as possible to second terminal end 102 without interfering with the mechanics of removing and attaching urine bag 9901. In some embodiments, Step 5 may be optional.

In various methods, the clamping step may be replaced with a capping step. When urine bag 9901 may be changed by removing urine bag 9901 and replacing urine bag 9901 with a new urine bag, second terminal end 102 may be capped shut with a cap, preferably a sterile cap, prior to removal of urine bag 9901. The cap may remain in place until the new urine bag may be attached to second terminal end 102 at which point the cap may be removed.

FIG. 7A through and including FIG. 7K may at least depict an embodiment of a connector-with-integrated-check-valve 700 or may depict components of connector-with-integrated-check-valve 700. In some embodiments, connector-with-integrated-check-valve 700 may be a dual ended connector with an integral check-valve disposed between the opposing tubing connection regions; wherein that integral check-valve may prevent urine reflux (backflow). The dual connector aspect may allow for connecting one end of connector-with-integrated-check-valve 700 to catheter-tubing 9920 and the remaining other connector end to extension-tubing 9930. In some embodiments, catheter-tubing 9920 may be the exit tubing portion of catheter 9915. In some embodiments, extension-tubing 9930 may then lead to urine bag 9901, such as, but not limited to, leg urine bag 9901a or bed urine bag 9901b.

FIG. 7A may depict a perspective and longitudinal cross-sectional view of connector-with-integrated-check-valve 700 that may be attached to catheter-tubing 9920 at one end and attached to extension-tubing 9930 at the other end of connector-with-integrated-check-valve 700. FIG. 7B may also depict connector-with-integrated-check-valve 700, but shown in an exploded, perspective, and longitudinal cross-sectional view. FIG. 7C may also depict connector-with-integrated-check-valve 700, but shown in an exploded and a perspective view (not cross-sectional).

Discussing FIG. 7A, FIG. 7B, and FIG. 7C, in some embodiments, connector-with-integrated-check-valve 700 may comprise three parts that may be assembled together. In some embodiments these three parts may be connector-for-catheter-tubing 710, connector-for-extension-tubing 730, and a gate 750.

Continuing discussing FIG. 7A, FIG. 7B, and FIG. 7C, in some embodiments, connector-for-catheter-tubing 710 may be removably attachable to catheter-tubing 9920 at a first-barb-region 712 of connector-for-catheter-tubing 710. In some embodiments, connector-for-catheter-tubing 710 may be a first-elongate-member. In some embodiments, connector-for-catheter-tubing 710 may comprise a first-hollow-core 714 for passage of urine. In some embodiments, disposed opposite of first-barb-region 712 may be a mating-end 716 of connector-for-catheter-tubing 710.

Continuing discussing FIG. 7A, FIG. 7B, and FIG. 7C, in some embodiments, connector-for-catheter-tubing 710 may be rigid or semi-rigid. In such embodiments, connector-for-catheter-tubing 710 may be injection molded and/or 3D printed from one or more thermoformed plastics. In such embodiments, connector-for-catheter-tubing 710 may be transparent or substantially transparent, which may aid in facilitating visual inspections for defects, biofilms, and the like. In such embodiments, connector-for-catheter-tubing 710 may be colored, such as, but not limited to, white.

Continuing discussing FIG. 7A, FIG. 7B, and FIG. 7C, in some embodiments, connector-for-catheter-tubing 710 may be an elongate member (e.g., the first-elongate-member) that may be radially symmetrical with respect to a longitudinal central axis of connector-for-catheter-tubing 710. Continuing discussing FIG. 7A, FIG. 7B, and FIG. 7C, first-barb-region 712 may be tiered. In some embodiments, first-barb-region 712 may be tiered hose-barbs.

Continuing discussing FIG. 7A, FIG. 7B, and FIG. 7C, in some embodiments, connector-for-catheter-tubing 710 may comprise a central-flange 720. In some embodiments, central-flange 720 may be is externally located and annular. In some embodiments, central-flange 720 may be located between first-barb-region 712 and mating-end 716. In some embodiments, central-flange 720 may help to facilitate disassembly of catheter-tubing 9920 from first-barb-region 712 of connector-for-catheter-tubing 710; e.g., by the user grabbing central-flange 720 in one hand and grabbing catheter-tubing 9920 in the other hand and pulling apart.

Continuing discussing FIG. 7A, FIG. 7B, and FIG. 7C, in some embodiments, connector-for-extension-tubing 730 may be attachable to extension-tubing 9930 at a second-barb-region 732 of connector-for-extension-tubing 730. In some embodiments, connector-for-extension-tubing 730 may be a second-elongate-member. In some embodiments, connector-for-extension-tubing 730 may comprise a second-hollow-core 734 for passage of the urine. In some embodiments, disposed opposite of second-barb-region 732 may be a complimentary-mating-end 736. In some embodiments, mating-end 716 (of connector-for-catheter-tubing 710) may be attached to complimentary-mating-end 736 (of connector-for-extension-tubing 730).

Continuing discussing FIG. 7A, FIG. 7B, and FIG. 7C, in some embodiments, connector-for-extension-tubing 730 may be rigid or semi-rigid. In such embodiments, connector-for-extension-tubing 730 may be injection molded and/or 3D printed from one or more thermoformed plastics. In such embodiments, connector-for-extension-tubing 730 may be transparent or substantially transparent, which may aid in facilitating visual inspections for defects, bio-films, and the like.

Continuing discussing FIG. 7A, FIG. 7B, and FIG. 7C, in some embodiments, connector-for-extension-tubing 730 may be an elongate member (e.g., the second-elongate-member) that may be radially symmetrical with respect to a longitudinal central axis of connector-for-extension-tubing 730.

Continuing discussing FIG. 7A, FIG. 7B, and FIG. 7C, in some embodiments, second-barb-region 732 may be tiered. In some embodiments, second-barb-region 732 may be tiered hose-barbs.

Continuing discussing FIG. 7A, FIG. 7B, and FIG. 7C, in some embodiments, connector-for-extension-tubing 730 may comprise a flange 738. In some embodiments, flange 738 may be externally located and annular. In some embodiments flange 738 may be located away from second-barb-region 732.

Continuing discussing FIG. 7A, FIG. 7B, and FIG. 7C, in some embodiments, gate 750 may be comprise one or more of the following properties: may be a circular disc; may be disc shaped; may be substantially disc shaped; may be a solid member; may be flexible; may be elastomeric; may be constructed from silicone; may be constructed from rubber; may be radially symmetrical; and/or the like. In some embodiments, gate 750 may be a circular shaped disc, that may be elastomeric, and flexible.

Continuing discussing FIG. 7A, FIG. 7B, and FIG. 7C, in some embodiments, when the connector-for-catheter-tubing 710 may be attached to the connector-for-extension-tubing 730 (e.g., via a union of mating-end 716 to complimentary-mating-end 736), with the gate 750 disposed between portions of connector-for-catheter-tubing 710 and portions of connector-for-extension-tubing 730; then connector-with-integrated-check-valve 700 may be formed from the connector-for-catheter-tubing 710, the connector-for-extension-tubing 730, and the gate 750.

Continuing discussing FIG. 7A, FIG. 7B, and FIG. 7C, in some embodiments, connector-with-integrated-check-valve 700 may permits urine flow is a desired-direction 770 from connector-for-catheter-tubing 710 towards connector-for-extension-tubing 730. Whereas, in some embodiments, connector-with-integrated-check-valve 700 may close and prevent backflow (reflux) of the urine in a direction from connector-for-extension-tubing 730 towards connector-for-catheter-tubing 710 when the urine exerts backflow pressure against gate 750, which may push gate 750 against a seat 718 that may be located within connector-for-catheter-tubing 710. In some embodiments, seat 718 may be structure of connector-for-catheter-tubing 710 located on or in first-hollow-core 714. In some embodiments, seat 718 may be an internal annular shelf located in first-hollow-core 714. In some embodiments, seat 718 may stop movement of gate 750. In some embodiments, seat 718 may form a seal with proximate portions of gate 750 when connector-with-integrated-check-valve 700 may be in the closed configuration.

FIG. 7D and FIG. 7E may depict connector-with-integrated-check-valve 700 in an open configuration. FIG. 7D may depict connector-with-integrated-check-valve 700, shown in a longitudinal cross-sectional view. FIG. 7E may be a close up view of connector-with-integrated-check-valve 700 shown in FIG. 7D. In the open configuration, gate 750 may not be touching seat 718.

Discussing FIG. 7E, FIG. 7B, and FIG. 7C, in some embodiments, connector-for-extension-tubing 730 may comprise catch-arms 740. In some embodiments, connector-for-extension-tubing 730 may comprise from two, three, four, five, or six catch-arms 740. In some embodiments, connector-for-extension-tubing 730 may comprise four catch-arms 740. In some embodiments, catch-arms 740 may be arranged radially with respect to a center of connector-for-extension-tubing 730 (see e.g., FIG. 7J). In some embodiments, a given catch-arm 740 may be a structural protrusion into a portion of the second-hollow-core 734 that may allow urine flow through second-hollow-core 734 but wherein the catch-arms 740 may be sized in relation to gate 750 to prevent the gate 750 from passing through a region of second-hollow-core 734 that is closest to second-barb-region 732. In some embodiments, catch-arms 740 may stop movement of gate 750 in desired-direction 770 from passing into or beyond second-barb-region 732. In some embodiments, catch-arms 740 may act as guides for some movement of gate 750.

Discussing FIG. 7E, FIG. 7B, and FIG. 7C, in some embodiments, each catch-arm 740 may comprise a support-surface 742. See also, FIG. 7J and FIG. 7K. In some embodiments, support-surface 742 may be located closer to complimentary-mating-end 736 than to second-barb-region 732. In some embodiments, support-surface 742 may be disposed opposite from seat 718 and facing the seat 718. In some embodiments, disposed between seat 718 and support-surface 742 may be a pocket 752 that may house gate 750. See e.g., FIG. 7E for pocket 752. In some embodiments, support-surface 742 may contact portions of gate 750 when the urine is flowing in desired-direction 770. In some embodiments, when the urine is flowing desired-direction 770 this direction of flow may create pressure upon gate 750, wherein this may push gate 750 against support-surfaces 742, which may be open configuration shown in FIG. 7E and in FIG. 7D. Urine may flow around the arm structures of catch-arms 740 through first-hollow-core 714.

Discussing FIG. 7E, FIG. 7B, and FIG. 7C, in some embodiments, each catch-arm 740 may comprise a post 746. In some embodiments, post 746 may protrude away from support-surface 742. See also, FIG. 7J and FIG. 7K.

Discussing FIG. 7E, FIG. 7B, and FIG. 7C, in some embodiments, gate 750 may float within pocket 752 of connector-with-integrated-check-valve 700. See FIG. 7E for pocket 752. In some embodiments, pocket 752 may be longitudinally bounded by seat 718 at one end of pocket 752 and by support-surfaces 742 at a remaining end of pocket 752. In some embodiments, support-surfaces 742 may be disposed opposite of seat 718 and may face seat 718. In some embodiments, support-surfaces 742 may be supportive surfaces of catch-arms 740. In some embodiments, catch-arms 740 may permit the urine flow through second-hollow-core 734 but may not permit passage of gate 750 into portions of second-hollow-core 734. In some embodiments, gate 750 may translate in pocket 752, between the open configuration and the closed configuration.

FIG. 7F and FIG. 7G may depict connector-with-integrated-check-valve 700 in the closed configuration. FIG. 7F may depict connector-with-integrated-check-valve 700, shown in a longitudinal cross-sectional view. FIG. 7G may be a close up view of connector-with-integrated-check-valve 700 shown in FIG. 7F. In the closed configuration, gate 750 may be touching seat 718. In the closed configurations, portions of gate 750 closest to seat 718 may be physically touching portions of seat 718.

FIG. 7H may depict connector-with-integrated-check-valve 700, shown in a perspective view, an assembled perspective view; wherein connector-with-integrated-check-valve 700 may be attached to catheter-tubing 9920 and attached to extension-tubing 9930.

FIG. 7I may show an outlet perspective view of connector-for-catheter-tubing 710, which may be a component of connector-with-integrated-check-valve 700. In some embodiments, FIG. 7I may depict a system for minimizing microbial migration to catheter-tubing. In some embodiments, this system may comprise extension-tubing 9930 of a predetermined length and connector-with-integrated-check-valve 700 attached to that predetermined length of extension-tubing 9930.

FIG. 7J may show an inlet view of connector-for-extension-tubing 730, which may be a component of connector-with-integrated-check-valve 700. FIG. 7K may depict an inlet perspective view of the connector-for-extension-tubing 730. In some embodiments, a distance between opposing posts 746 may be receiving-distance 744. See FIG. 7J for receiving-distance 744. In some embodiments, gate 750 may comprise a gate-outside-diameter 754 which may be an outside diameter of gate 750. See FIG. 7C for gate-outside-diameter 754. In some embodiments, gate-outside-diameter 754 may be less than receiving-distance 744; and in this relationship, portions of catch-arms 740 (e.g., spaced posts 746) may help to guide movement of gate 750 within pocket 752.

In some embodiments, mating-end 716 (of connector-for-catheter-tubing 710) may be a protruding annular ring that may protrude in a direction away from the first-barb-region 712. See e.g., FIG. 7I, FIG. 7B, FIG. 7E, and FIG. 7G. In some embodiments, complimentary-mating-end 736 may be a ring shaped receiving channel sized to receive the protruding annular ring of mating-end 716. For complimentary-mating-end 736 see FIG. 7J, FIG. 7K, FIG. 7B, FIG. 7E, and FIG. 7G. In some embodiments, this ring shaped receiving channel of complimentary-mating-end 736 may be located in flange 738. See e.g., FIG. 7B. In some embodiments, attachment between mating-end 716 and complimentary-mating-end 736 may be by one or more of: ultrasonic welding, heat welding, solvent bonding, chemical adhesive, snap fit, friction fit, press fit, and/or the like.

FIG. 8 may depict a perspective and longitudinal cross-sectional view of an embodiment of a connector-with-integrated-check-valve 800. Functionally, connector-with-integrated-check-valve 800 may differ from connector-with-integrated-check-valve 700, in that the check-valve aspect of connector-with-integrated-check-valve 800 may be typically closed unless normal urine flow in desired-direction 770 opens the check-valve. Whereas, the check-valve aspect of connector-with-integrated-check-valve 700 may be normally open unless there is urine backflow (reflux) to close the integral check-valve. In some embodiments, such function of connector-with-integrated-check-valve 800 may be achieved by use of a spring, closing-spring 845, in the pocket, pocket 852. This closing-spring 845 may always be pressing against gate 750.

Discussing FIG. 8, in some embodiments, connector-with-integrated-check-valve 800 may comprise four parts, that of: connector-for-catheter-tubing 710, gate 750, connector-for-extension-tubing 830, and closing-spring 852. Structurally and functionally, gate 750 may be as discussed above for gate 750 in connector-with-integrated-check-valve 700. Structurally and functionally, connector-for-catheter-tubing 710 may be as discussed above for connector-for-catheter-tubing 710 in connector-with-integrated-check-valve 700; with the exception that now connector-for-catheter-tubing 710 is attached to connector-for-extension-tubing 830 and not connector-for-extension-tubing 730.

Continuing discussing FIG. 8, in some embodiments, connector-for-extension-tubing 830 may be attachable to extension-tubing 9930 at a second-barb-region 832 of connector-for-extension-tubing 830. In some embodiments, connector-for-extension-tubing 830 may be a second-elongate-member. In some embodiments, connector-for-extension-tubing 830 may comprise a second-hollow-core 834 for passage of the urine. In some embodiments, disposed opposite of second-barb-region 832 may be a complimentary-mating-end 836. In some embodiments, mating-end 716 (of connector-for-catheter-tubing 710) may be attached to complimentary-mating-end 836 (of connector-for-extension-tubing 830).

Continuing discussing FIG. 8, in some embodiments, connector-for-extension-tubing 830 may be rigid or semi-rigid. In such embodiments, connector-for-extension-tubing 830 may be injection molded and/or 3D printed from one or more thermoformed plastics. In such embodiments, connector-for-extension-tubing 830 may be transparent or substantially transparent, which may aid in facilitating visual inspections for defects, biofilms, and the like.

Continuing discussing FIG. 8, in some embodiments, connector-for-extension-tubing 830 may be an elongate member (e.g., the second-elongate-member) that may be radially symmetrical with respect to a longitudinal central axis of connector-for-extension-tubing 830.

Continuing discussing FIG. 8, in some embodiments, second-barb-region 832 may be tiered. In some embodiments, second-barb-region 832 may be tiered hose-barbs.

Continuing discussing FIG. 8, in some embodiments, connector-for-extension-tubing 830 may comprise a flange 838. In some embodiments, flange 838 may be externally located and annular. In some embodiments flange 838 may be located away from second-barb-region 832.

Continuing discussing FIG. 8, in some embodiments, about mid-way along second-hollow-core 834, inside of connector-for-extension-tubing 830, may be spring-stops 840; wherein "about" in this context may be plus or minus 25% of the length of connector-for-extension-tubing 830. In some embodiments, spring-stops 840 may be protrusions into second-hollow-core 834, that do not prevent urine flow. In some embodiments, disposed between spring-stops 840 and seat 718 (of connector-for-catheter-tubing 710), may be pocket 852. In some embodiments, closing-spring 845 and gate 750 may be located within pocket 852. In some embodiments, closing-spring 845 may be touching portions of spring-stops 840 and touching portions of gate 750. In some embodiments, gate 750 may be removably touching seat 718 and touching an end of closing-spring 845. In some embodiments, when there is normal urine flow in desired-direction 770, such normal urine pressure may press against gate 750, which in turn may then press against closing-spring desired-direction 770, which opens this integral check-valve and allows normal urine flow into extension-tubing 9930. When such normal urine flow ceases, then closing-spring 845 may then close gate 750 against seat 718, to close this integral check-valve.

FIG. 9A may depict a perspective and longitudinal cross-sectional view of an embodiment of a connector-with-integrated-check-valve 900. FIG. 9B may depict connector-with-integrated-check-valve 900, but shown in an exploded and a perspective view. Functionally, connector-with-integrated-check-valve 900 may differ from connector-with-integrated-check-valve 700, in that the check-valve aspect of connector-with-integrated-check-valve 900 may be typically closed unless normal urine flow in desired-direction 770 opens the check-valve. Whereas, the check-valve aspect of connector-with-integrated-check-valve 700 may be normally open unless there is urine backflow (reflux) to close the integral check-valve. In some embodiments, such function of connector-with-integrated-check-valve 900 may be achieved by use of a hinge gate, i.e., a flapper gate, as in gate 950, in the pocket, pocket 940.

Discussing FIG. 9A and FIG. 9B, in some embodiments, connector-with-integrated-check-valve 800 may comprise three parts, that of: connector-for-catheter-tubing 710, gate 950, and connector-for-extension-tubing 930. Structurally and functionally, gate 950 may be as discussed above for gate 750 in connector-with-integrated-check-valve 700; except gate 950 may comprise additional structure, that of hinge 956. In some embodiments, gate 950 may be a substantially circular shaped disc, with the extension of hinge 956, that may be elastomeric, and flexible. Structurally and functionally, connector-for-catheter-tubing 710 may be as discussed above for connector-for-catheter-tubing 710 in connector-with-integrated-check-valve 700; with the exception that now connector-for-catheter-tubing 710 is attached to connector-for-extension-tubing 930 and not connector-for-extension-tubing 730.

Discussing FIG. 9A and FIG. 9B, in some embodiments, connector-for-extension-tubing 930 may be attachable to extension-tubing 9930 at a second-barb-region 932 of connector-for-extension-tubing 930. In some embodiments, connector-for-extension-tubing 930 may be a second-elongate-member. In some embodiments, connector-for-extension-tubing 930 may comprise a second-hollow-core 934 for passage of the urine. In some embodiments, disposed opposite of second-barb-region 932 may be a complimentary-mating-end 936. In some embodiments, mating-end 716 (of connector-for-catheter-tubing 710) may be attached to complimentary-mating-end 936 (of connector-for-extension-tubing 930).

Discussing FIG. 9A and FIG. 9B, in some embodiments, connector-for-extension-tubing 930 may be rigid or semi-rigid. In such embodiments, connector-for-extension-tubing 930 may be injection molded and/or 3D printed from one or more thermoformed plastics. In such embodiments, connector-for-extension-tubing 930 may be transparent or substantially transparent, which may aid in facilitating visual inspections for defects, biofilms, and the like.

Discussing FIG. 9A and FIG. 9B, in some embodiments, connector-for-extension-tubing 930 may be an elongate member (e.g., the second-elongate-member) that may be radially symmetrical with respect to a longitudinal central axis of connector-for-extension-tubing 930.

Discussing FIG. 9A and FIG. 9B, in some embodiments, in some embodiments, second-barb-region 932 may be tiered. In some embodiments, second-barb-region 932 may be tiered hose-barbs.

Discussing FIG. 9A and FIG. 9B, in some embodiments, connector-for-extension-tubing 930 may comprise a flange 938. In some embodiments, flange 938 may be externally located and annular. In some embodiments flange 938 may be located away from second-barb-region 932.

Discussing FIG. 9A and FIG. 9B, in some embodiments, proximate to complimentary-mating-end 936, inside of connector-for-extension-tubing 930, may be stop 942; wherein "proximate" in this context may be plus or minus 25% of the length of connector-for-extension-tubing 930. In some embodiments, stop 942 may be a narrowing of an inside diameter of second-hollow-core 934, that does not prevent urine flow, but that is narrower than gate-outside-diameter 954 of gate 950, which may prevent passage of gate 950 into portions of second-hollow-core 934. In some embodiments, disposed between stop 942 and seat 718 (of connector-for-catheter-tubing 710), may be pocket 940. In some embodiments, gate 950 may be located within pocket 852. In some embodiments, gate 950 may be removably touching seat 718. In some embodiments, pocket 940 may be a hollow cylinder. In some embodiments at a distal end of pocket 940 may be a notch, a hinge-receiver 944 for receiving hinge 956 of gate 950. In some embodiments, around a perimeter of gate 950 may be an extending tab, that of hinge 956. In some embodiments, this tab of hinge 956 may fit into the notch of hinge-receiver 944. In this way, gate 950 may removably rest against seat 718 when where there is no urine flow; and when there is urine flow in desired-direction 770, then such urine pressure against gate 950 may cause portions of gate 950 to bend towards stop 942 and to stop at stop 942, allowing urine to flow to extension-tubing 9930 through portions of second-hollow-core 934.

In some embodiments, attachment between mating-end 716 and complimentary-mating-end (e.g., 736, 836, or 936) may be by one or more of: ultrasonic welding, heat welding, solvent bonding, chemical adhesive, snap fit, friction fit, press fit, and/or the like. In some embodiments, such attachment may be intended to be permanent. In some embodiments, such attachment may be intended to be removable.

In some embodiments, at least some of internal wettable surfaces of connector-with-integrated-check-valve 700 or of connector-with-integrated-check-valve 800 or of connector-with-integrated-check-valve 900 may be coated with an antimicrobial coating. In some embodiments, at least some of internal wettable surfaces of connector-with-integrated-check-valve 700 or of connector-with-integrated-check-valve 800 or of connector-with-integrated-check-valve 900 may be treated with an antimicrobial product. Such antimicrobial coatings and/or treatments may help to prevent or minimize microbial colonization of the internal wettable surfaces. Such antimicrobial coatings and/or treatments may help to prevent or minimize biofilm adhesion to the internal wettable surfaces.

In some embodiments, any check-valve shown in FIG. 1A through FIG. 6H may be replaced with connector-with-integrated-check-valve (700, 800, and/or 900).

Note, in some embodiments, if a clamp is positioned around extension-tubing 9930, and if said clamp is closed preventing any air into extension-tubing 9930 above the clamp, and prior to disengaging extension-tubing 9930 from the urine collection device urine bag 9901 use of such a clamp would maintain a closed-system above the clamp which would also include a closed-system with respect to catheter 9915.

A tubing for minimizing undesirable microbial migration, as well as a system and method for forming and maintaining a closed-system of urinary tubing have been described. A connector-with-integrated-check-valve has also been described. The foregoing description of the various embodiments of the invention has been presented for the purposes of illustration and disclosure. It is not intended to be exhaustive or to limit the invention to the precise form disclosed. Many modifications and variations are possible in light of the above teaching without departing from the spirit of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A system configured for helping to prevent urinary tract infections in a patient using a urinary catheter by preventing urine backflow into the urinary catheter, wherein the system comprises:

urinary extension-tubing configured for transporting urine from the urinary catheter to a urine collection device, wherein the urinary extension-tubing comprises two opposing terminal ends; and a connector-with-integrated-check-valve that is attached to one of the two opposing terminal-ends of the urinary extension-tubing, wherein the connector-with-integrated-check-valve comprises:

a connector-for-catheter-tubing that is removably attachable to the urinary catheter at a first-barb-region of the connector-for-catheter-tubing; wherein the connector-for-catheter-tubing is a first-elongate-member; wherein the connector-for-catheter-tubing comprises a first-hollow-core configured for passage of urine; wherein disposed opposite of the first-barb-region is a mating-end that is an annular ring protrusion extending away from the first-barb-region;

a connector-for-extension-tubing that is attached to the urinary extension-tubing at a second-barb-region of the connector-for-extension-tubing; wherein the connector-for-extension-tubing is a second-elongate-member; wherein the connector-for-extension-tubing comprises a second-hollow-core configured for passage of the urine; wherein disposed opposite of the second-barb-region is a complimentary-mating-end that is an inset receiving channel within a flange of the connector-for-extension-tubing; wherein the mating-end is attached to the complimentary-mating-end by the mating-end fitting within the complimentary-mating-end such that sides of the mating-end are entirely within the receiving-channel and the sides of the mating-end are not touching a gate; and the gate that is a disk shaped radially symmetrical cylindrical member, wherein the gate is free of openings and free of circumferential bulges, wherein the gate is non-magnetically operable, not intended to be pierced by a needle in operation, and is substantially non-deformable in operation;

wherein when the connector-for-catheter-tubing is attached to the connector-for-extension-tubing by the mating-end fitting within the complimentary-mating-end, the gate is disposed between portions of the connector-for-catheter-tubing and portions of the connector-for-extension-tubing such that the gate is freely back and forth movable within these portions; the connector-with-integrated-check-valve is formed from the connector-for-catheter-tubing, the connector-for-extension-tubing, and the gate; wherein the connector-with-integrated-check-valve does not impede urine flow from the patient urinating into the urinary catheter in a desired-direction from the connector-for-catheter-tubing towards the connector-for-extension-tubing; wherein the connector-with-integrated-check-valve closes and prevents backflow of the urine in a direction from the connector-for-extension-tubing towards the connector-for-catheter-tubing when urine in the urinary extension-tubing exerts backflow pressure against the gate, which pushes the gate against a seat that is a flat annular shelf located within and part of the connector-for-catheter-tubing, such that the portions of the connector-for-catheter-tubing comprises the seat.

2. The system according to claim 1, wherein the connector-for-catheter-tubing is rigid.

3. The system according to claim 1, wherein the connector-for-catheter-tubing comprises a central-flange that is externally located and annular; wherein this central-flange is located between the first-barb-region and the mating-end.

4. The system according to claim 1, wherein the connector-for-extension-tubing is rigid.

5. The system according to claim 1, wherein the connector-for-extension-tubing comprises catch-arms; wherein the catch-arms are structural protrusions into portions of the second-hollow-core that allow urine flow through the second-hollow-core but wherein the catch-arms are sized in relation to the gate to prevent the gate from passing through a region of the second-hollow-core that is closest to the second-barb-region.

6. The system according to claim 5, wherein each catch-arm comprises a support-surface; wherein the support-surface is located closer to the complimentary-mating-end than to the second-barb-region; wherein the support-surface is disposed opposite from the seat and facing the seat; wherein disposed between the seat and the support-surface is a pocket that houses the gate; wherein the support-surface contacts portions of the gate when urine is flowing in the desired-direction.

7. The system according to claim 6, wherein each catch-arm comprises a post; wherein the post protrudes away from the support-surface; wherein the posts bound sides of the gate.

8. The system according to claim 1, wherein the gate comprises one or more of the following properties: is a solid member; is flexible; is elastomeric; is constructed from silicone; or is constructed from rubber.

9. The system according to claim 1, wherein the gate floats and translates within a pocket of the connector-with-integrated-check-valve; wherein the pocket is longitudinally bounded by the seat at one end of the pocket and by support-surfaces at a remaining end of the pocket; wherein the support-surfaces are disposed opposite of the seat and face the seat; wherein the support-surfaces are supportive surfaces of catch-arms and the catch-arms are structural protrusions into a portion of the second-hollow-core; wherein the connector-for-extension-tubing comprises the catch-arms; wherein the catch-arms permit urine flow through the second-hollow-core but do not permit passage of the gate into the portion of the second-hollow-core; wherein the pocket is bounded on its sides by posts, wherein the posts protrude away from the supportive-surfaces towards the seat; wherein each catch-arm comprises a post.

10. The system according to claim 1, wherein the gate has a gate-outside-diameter that is less than a receiving-distance between posts of opposing catch-arms, wherein the portions of the connector-for-extension-tubing comprises the catch-arms.

11. The system according to claim 1, wherein attachment between the mating-end and the complimentary-mating-end is by one or more of: ultrasonic welding, heat welding, solvent bonding, chemical adhesive, snap fit, friction fit, or press fit.

12. The system according to claim 1, wherein at least some of internal wettable surfaces of the connector-with-integrated-check-valve are coated with an antimicrobial coating.

13. The system according to claim 1, wherein at least some of internal wettable surfaces of the connector-with-integrated-check-valve are treated with an antimicrobial product.

14. The system according to claim 1, wherein the connector-with-integrated-check-valve has only two openings for urine flow, one inlet and one outlet, respectively; wherein the one inlet is at an end of the first-barbed-region leading to the first-hollow-core; and wherein the one outlet is at an end of the second-barbed-region.

15. The system according to claim 1, wherein the connector-for-catheter-tubing comprises a central-flange that is an external annular ring around the connector-for-catheter-tubing; wherein the flange of connector-for-extension-tubing and the central-flange of connector-for-catheter-tubing have substantially the same outer diameter.

16. The system according to claim 1, wherein the connector-for-catheter-tubing is free of ribs.

17. The system according to claim 1, wherein the urinary extension-tubing is free of side ports.

18. The system according to claim 1, wherein the first-barb-region and the second-barb-region are male connectors.

19. The system according to claim 1, wherein the urinary extension-tubing is of a fixed and predetermined length.

20. The system according to claim 1, wherein a default position of the connector-with-integrated-check-valve is open, when there is no urine backflow pressure pushing the gate towards the seat.

21. The system according to claim 1, wherein the urinary catheter, that the connector-for-catheter-tubing is attachable to, is either an indwelling catheter or an external catheter.

* * * * *